US005695759A

United States Patent [19]
Good et al.

[11] Patent Number: 5,695,759
[45] Date of Patent: Dec. 9, 1997

[54] METHODS AND COMPOSITIONS FOR ATTENUATING ANTIBODY-MEDIATED XENOGRAFT REJECTION IN HUMAN RECIPIENTS

[75] Inventors: A. Heather Good, Edmonton, Canada; David K. C. Cooper, Oklahoma City, Okla.; Andrew J. Malcolm, Edmonton, Canada

[73] Assignees: Alberta Research Council, Edmonton, Canada; Integris Baptist Medical Ctr., Oklahoma City, Okla.

[21] Appl. No.: 459,405

[22] Filed: Jun. 2, 1995

Related U.S. Application Data

[60] Division of Ser. No. 933,466, Aug. 21, 1992, which is a continuation-in-part of Ser. No. 749,529, Aug. 23, 1991, abandoned.

[51] Int. Cl.$^6$ .............................. C07H 3/04; C07H 3/06; C07H 5/06
[52] U.S. Cl. ................. 424/140.1; 536/4.1; 536/17.2; 536/22.1; 536/55.2
[58] Field of Search ..................... 530/413; 536/4.1, 536/17.2, 22.1, 55.2; 424/140.1

[56] References Cited

U.S. PATENT DOCUMENTS

| | | | |
|---|---|---|---|
| 4,137,401 | 1/1979 | Lemieux et al. | 536/116 |
| 4,238,473 | 12/1980 | Lemieux et al. | 424/11 |
| 4,362,720 | 12/1982 | Lemieux et al. | 424/180 |
| 5,079,353 | 1/1992 | Ratcliffe et al. | 536/53 |
| 5,149,425 | 9/1992 | Mazid | 210/198.2 |

FOREIGN PATENT DOCUMENTS

| | | |
|---|---|---|
| 0371636 | 6/1990 | European Pat. Off. |
| 1544908 | 4/1979 | United Kingdom |

OTHER PUBLICATIONS

R. Nowak, *Science*, 266, 1148–1151, 1994.
W. J. Herbert et al. *Dictionary of Immunology*—3rd Ed., Blackwell Scientific Publicatons, Oxford, UK, 1985, pp. 14 and 105.
I. M. Roitt, *Essential Immunology*—5th Ed., Blackwell Scientific Publications, Oxford, UK, 1984, p. 222.
*The Merck Manual*, 16th Ed., Berkow, et al. Eds. pp. 346–354.
Alexandre, et al., "Plasmapheresis and splenectomy in experimental renal xenotrasplantation", Xenograft, 25, pp. 259–266 (1989).
Caves, et al., "Hyperacute Rejection of Orthotopic Cardiac Allografts in Dogs Following Solubilized Antigen Pretreatment$^1$", Transpl., vol. 16, No. 3, pp.252–256 (1973).
Chien, et al., "Isolation and characterization of a heptaglycosylceramide from bovine erythrocyte membranes", J. of Lipid Res., vol. 20, pp.669–673 (1979).
Cox, et al., "A New Synthesis of 4–O–α–D–Galactopyranosyl–D–Galactopyranose", Carbohy. Res., vol. 62, pp.245–252 (1978).

Dahmen, et al., "Synthesis of Spacer–Arm, Lipid, and Ethyl Glycosides of The Trisaccharide Portion [α–D–Gal.(1→4)β–D–Gal–(1→4)–β–D–Glcl] of The Blood–Group P$^K$ Antigen: Preparation of Neoglycoproteins", Carbohy. Res., vol. 127, pp. 15–25 (1984).
Eto, et al., "Chemistry of Lipid of the Posthemolytic Residue or Stroma of Erythrocytes", J. Biochem., vol. 64, No. 2, pp.205–213 (1968).
Fischel, et al., "Prolonged Survival of a Discordant Cardiac Xenograft in a Rhesus Monkey", Transpl. Proc., vol. 23, No. 1, pp.589–590 (Feb. 1991).
Galili, et al., "Evolutionary relationship between the natural anti–Gal antibody and the Galα1→3Gal epitope in primates", Proc. Natl. Acad. Sci. USA, vol. 84, pp.1369–1373 (Mar. 1987).
Garegg, et al., "A Synthesis of 8–methoxycarbonyloct–1–yl O–α–D–Galactopyranosyl–(1→3)–O–β–D–Galactopyranosyl–(1→4)–2–Acetamido–2–Deoxy–β–D–Glucopyranoside", Carbohy. Res., vol. 136 pp.207–213 (1985).
Jacquinet, et al., "Synthesis of Blood–group Substances Part 11. Synthesis of the Trisaccharide O–α–D–galactopyranosyl–(1→3)–O–β–D–Galactopyranosyl–(1→4)–2–Acetamido–2–Deoxy–β–D–Glucopyranose", J. Chem. Soc. [Perkin I], pp.326–330 (1981).
Killion, "Carbohydrate interference of complement–dependent cell lysis", Experientia, vol. 43, pp.327–329 (1987).
Lalezari, et al., "Carbohydrate–Specific Antibodies in Normal Human Sera", Vox Sang. vol. 47, pp.133–145 (1984).
Palmer, et al., "Removal of Anti–HLA Antibodies by Extracorporeal Immunoadsorption to Enable Renal Transplantation", The Lancet, pp.10–12 (Jan. 7, 1989).
Pinto, et al., "Preparation of glycoconjugates for use as artificial antigens: A simplified procedure", Carbohy. res., vol. 124, pp.313–318 (1983).
Platt, et al., "Transplantation of discordant xenografts: a review of progress", Immun. Today, vol. 11, No. 12, pp.450–457 (1990).
Platt, et al., "Endothelial Cell Antigens Recognized by Xenoreactive Human Natural Antibodies", Transpl., vol. 50, pp.817–822 (Nov. 1990).
Rapp, et al., "Forssmann Antigen and Antibody: Preparation of Water Soluble Antigen and Measurement of Antibody Concentration by Precipitin Analysis, by C'la Fixation and by Hemolytic Activity", J. of Immun., vol. 96, 96, pp.913–919 (1966).

(List continued on next page.)

*Primary Examiner*—David Saunders
*Attorney, Agent, or Firm*—Burns, Doane, Swecker & Mathis, L.L.P.

[57] ABSTRACT

Antibody-mediated xenograft rejection is attenuated by (1) removing preformed antibodies to various identified carbohydrate xenoantigens from the recipient's circulation prior to transplantation by extracorporeal perfusion of the recipient's blood over a biocompatible solid support to which the xenoantigens are bound and/or (2) parenterally administering a xenoantibody-inhibiting amount of an identified xenoantigen to the recipient shortly before graft revascularization and thereafter.

7 Claims, 19 Drawing Sheets

OTHER PUBLICATIONS

Ratcliffe, et al., U.S. Patent Serial No. 07/278,106, Nov. 30, 1988.

Romano, et al., "Neutralization of ABO Blood Group Antibodies by Specific Oligosaccharides", Transpl. Proc., vol. XIX, No. 6, pp.4426–4430 (Dec. 1987).

Shons, et al., "Techniques of in vivo plasma modification for the treatment of hyperacute rejection", Surgery, vol. 73, No. 1, pp.20–37 (Jan. 1973).

Taube, et al., "Successful Removal and Prevention of Resynthesis of Anti–HLA ANtibody", Transpl., vol. 37, No. 3, pp.254–255 (1984).

Terman, et al., "Specific Suppression of Antibody Rebound After Extracorporeal Immunoadsorption", Clin. Exp. Immun., vol. 34, pp.32–41 (1978).

Terman, et al., "Modification of hyperacute renal xenograft rejection after extracorporeal immunoadsrption of heterospecific antibody", Int'l J. of Artif. Organs, vol. 2, No. , pp.35–41 (1979).

Terman, et al., "Specific removal of antibody by extracorporeal circulation over antigen immobilized in collodion–charcoal", Clin. Exp. Immun., vol. 28, pp.180–188 (1977).

Weetall, et al., "Immobilized Enzymes", Methods in Enzymology, Mosbach Ed., vol. XLIV, pp.140–146 (1976).

Wieslander, et al., "Specificity of Human Antibodies Against Galα1–3Gal Carbohydrate Epitope and Distinction from Natural Antibodies Reacting with Galα1–2Gal or Galα1–4Gal" Glycoconjugate J., vol. 7, pp.85–100 (1990).

Yoshioka, et al., "Attenuation of Hyperacute Xenograft Rejection in Unmodified Host by Extracorporeal Plasma Perfusion", Transpl. vol. 24, No. 1, pp.78–81 (1977).

W.I. Bensinger et al, Transfusion, 21, 335–342, 1991.

W.I. Benswiger et al, Transplantation, 33, 427–429, 1982.

W.I. Bensinger et al, Vox Sang., 48, 357–361, 1985.

Galili et al, Jour. Exper. Med., 162, 573–582, 1985.

Galili et al, Jour. Biol. Chem., 263, 17755–17762, 1988.

Laus et al, Int. Arch. Allergy Appl. Immun; 85, 201–207, 1988.

Van Breda Vriesman, Xenograft, 25, 267–271, 1989.

F.M. Bach, in D. K. C. Cooper et al (Eds.), *Xenotransplantation*, Springer–Verlag, 1991, pp. 81–98.

Barrett, J.T., "Biologic Aspects of the Immune Response", *Textbook of Immunology*, Third Ed., pp. 130–135 (1978).

Good, A.H., et al., "Identification of Carbohydrate Structures That Bind Human Antiporcine Antibodies: Implications for Discordant Xenografting in Humans", *Transplantation Proceedings*, 24(2):559–562, Apr., 1992.

Kolar, C., et al. "Preparation and Use of Synthetic Blood Group specific Immunoadsorbents", *Behring Inst. Mitt.*, No. 2:94–103 (1988).

Chembiomed, *Research Products*, available from the "Chembiomed Research Library".

Chembiomed, *Synsorb*, available from the "Chembiomed Research Library", 4 pages.

Chembiomed, *Syntype*, available from the "Chembiomed Research Library", 2 pages.

Chembiomed, *Synaff*, available from the "Chembiomed Research Library", 2 pages.

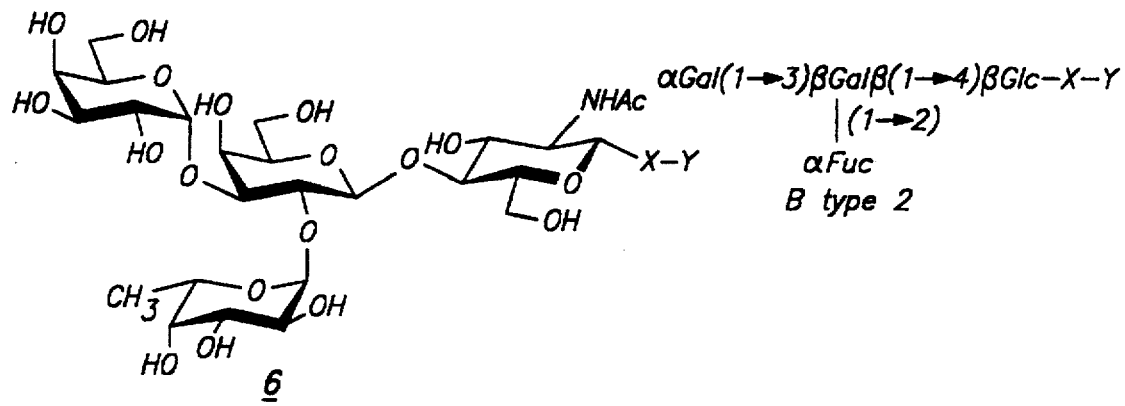
αGal(1→3)βGalβ(1→4)βGlc-X-Y
|(1→2)
αFuc
B type 2
6
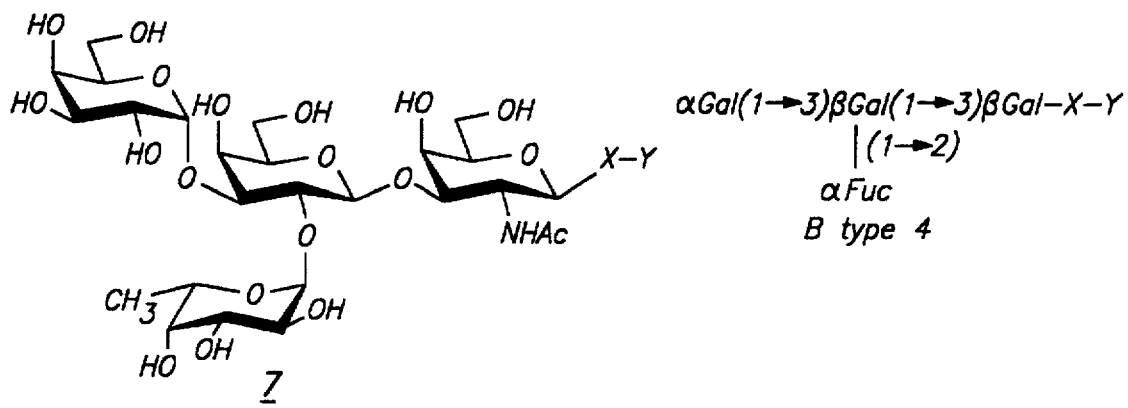
αGal(1→3)βGal(1→3)βGal-X-Y
|(1→2)
αFuc
B type 4
7
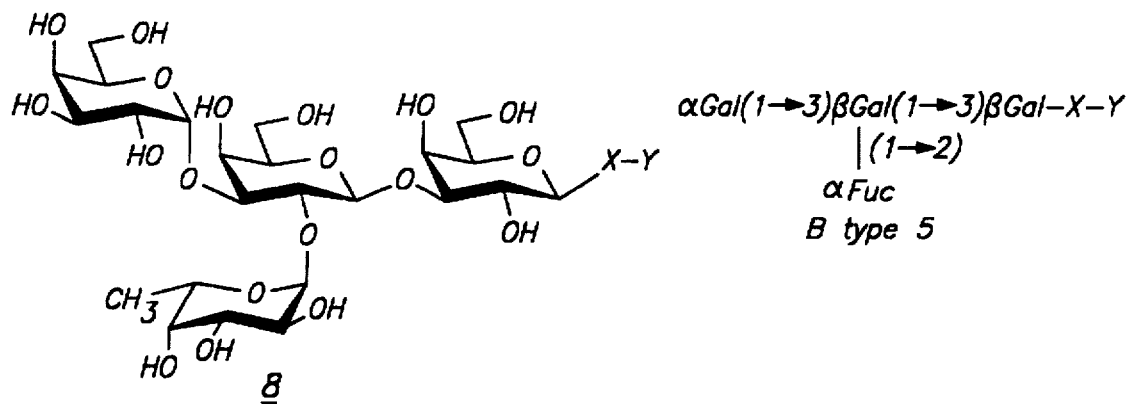
αGal(1→3)βGal(1→3)βGal-X-Y
|(1→2)
αFuc
B type 5
8
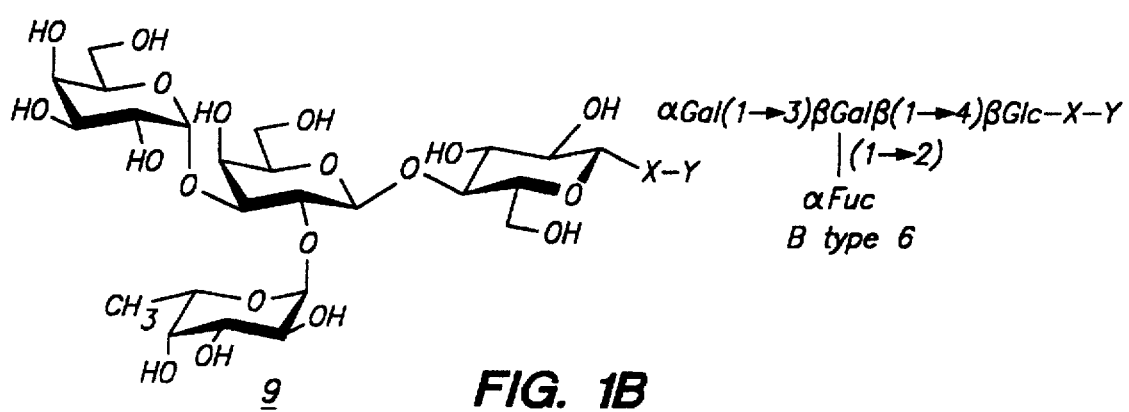
αGal(1→3)βGalβ(1→4)βGlc-X-Y
|(1→2)
αFuc
B type 6
9
FIG. 1B

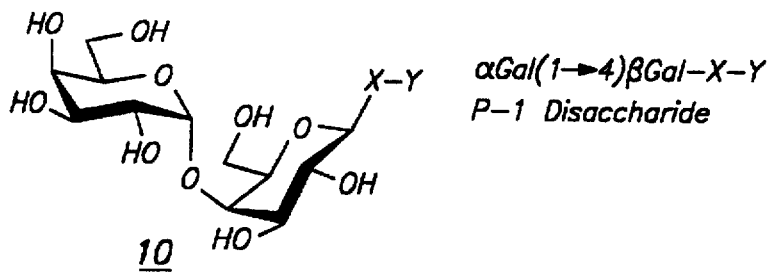
αGal(1→4)βGal-X-Y
P-1 Disaccharide
10
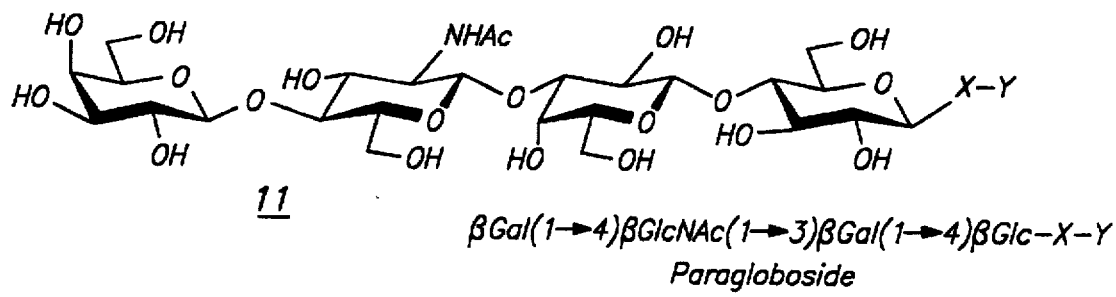
βGal(1→4)βGlcNAc(1→3)βGal(1→4)βGlc-X-Y
Paragloboside
11
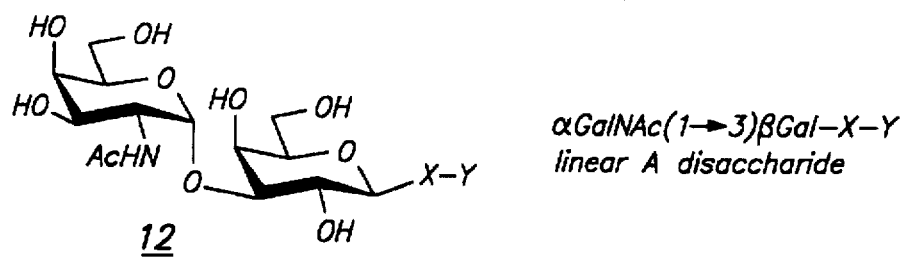
αGalNAc(1→3)βGal-X-Y
linear A disaccharide
12
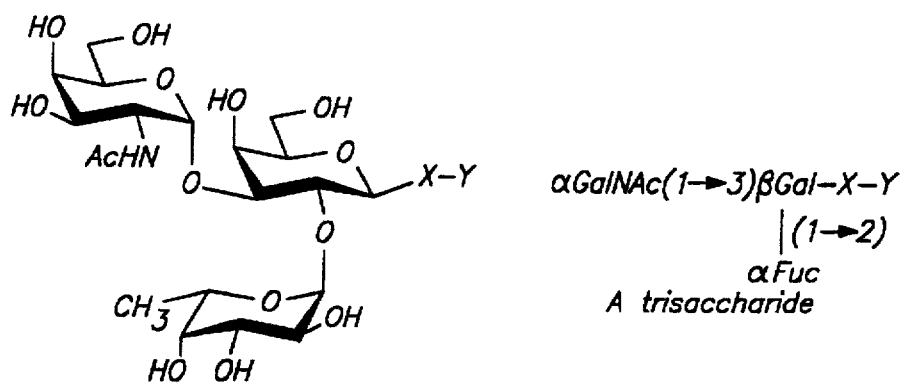
αGalNAc(1→3)βGal-X-Y
       |(1→2)
      αFuc
A trisaccharide
13
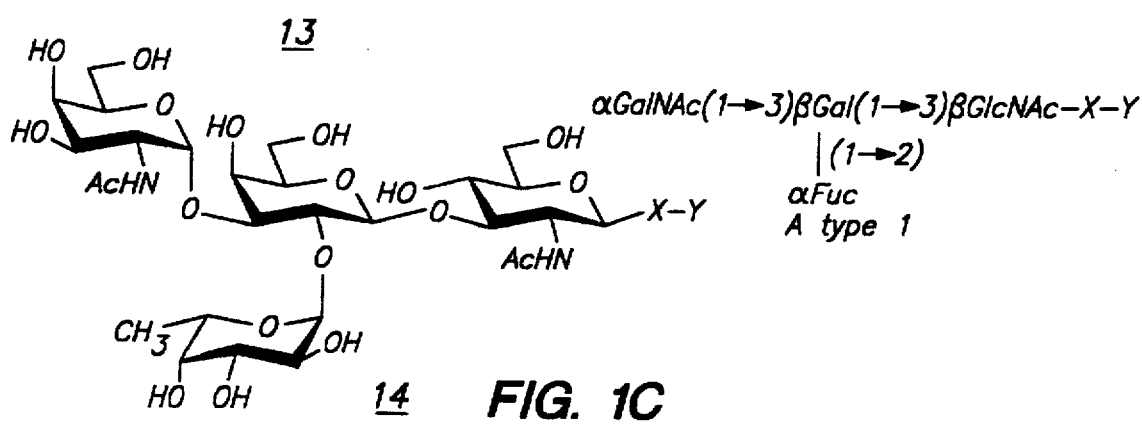
αGalNAc(1→3)βGal(1→3)βGlcNAc-X-Y
                |(1→2)
               αFuc
A type 1
14   FIG. 1C

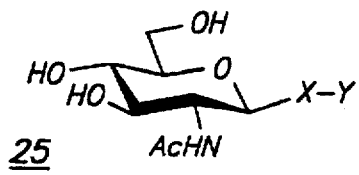
βGlcNAc-X-Y
N-acetyl-β-D-glucosamide
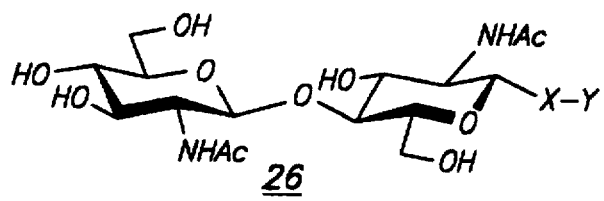
βGlcNAc(1→4)βGlcNAc-X-Y
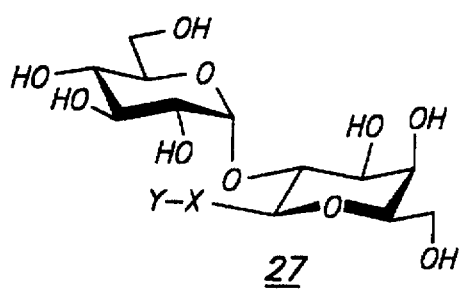
αGlc(1→2)βGal-X-Y
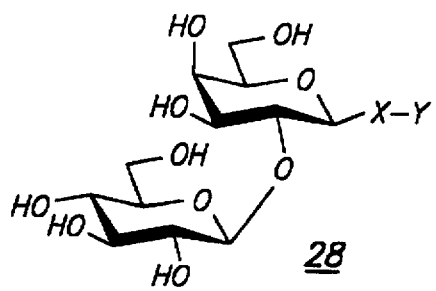
βGlc(1→2)βGal-X-Y
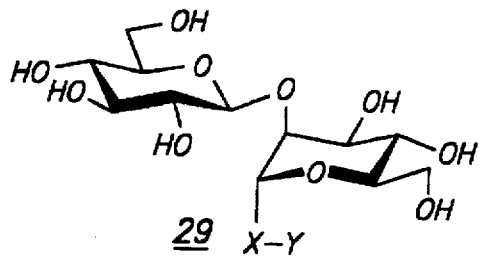
βGlc(1→2)αMan-X-Y
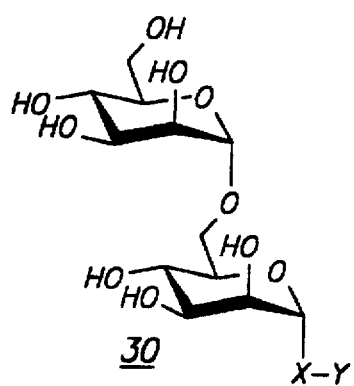
αMan(1→6)αMan-X-Y
FIG. 1F

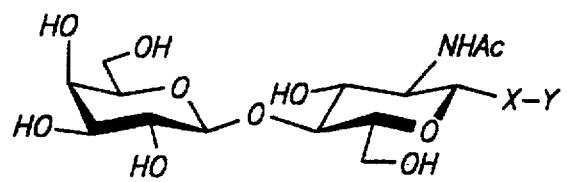
βGal(1→4)βGlcNAc-X-Y
LacNAc
36
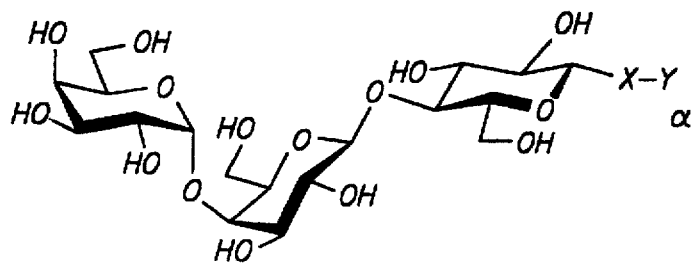
αGal(1→4)βGal(1→4)βGlc-X-Y
P-K Trisaccharide
37
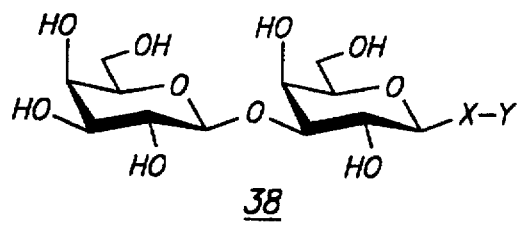
βGal(1→3)βGal-X-Y
38
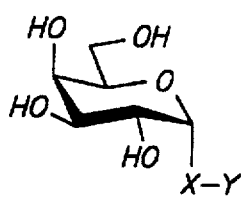
α-D-Gal-X-Y
α-D-galactoside
39
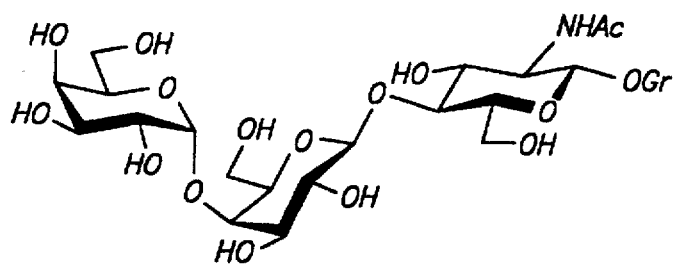
αGal(1→4)βGal(1→4)βGlcNAc
P-1 Trisaccharide
40
FIG. 1H

HUMAN PLASMA ADSORBED WITH SYNSORBS OR PIG HEART TISSUE
O PLASMA

AB PLASMA

▨ PIG KIDNEY CELLS   ⊠ PIG RBC   ☐ PIG LYMPHOCYTES
U=UNADSORBED PLASMA   P=CHROMOSORB P   PHT=PIG HEART TISSUE

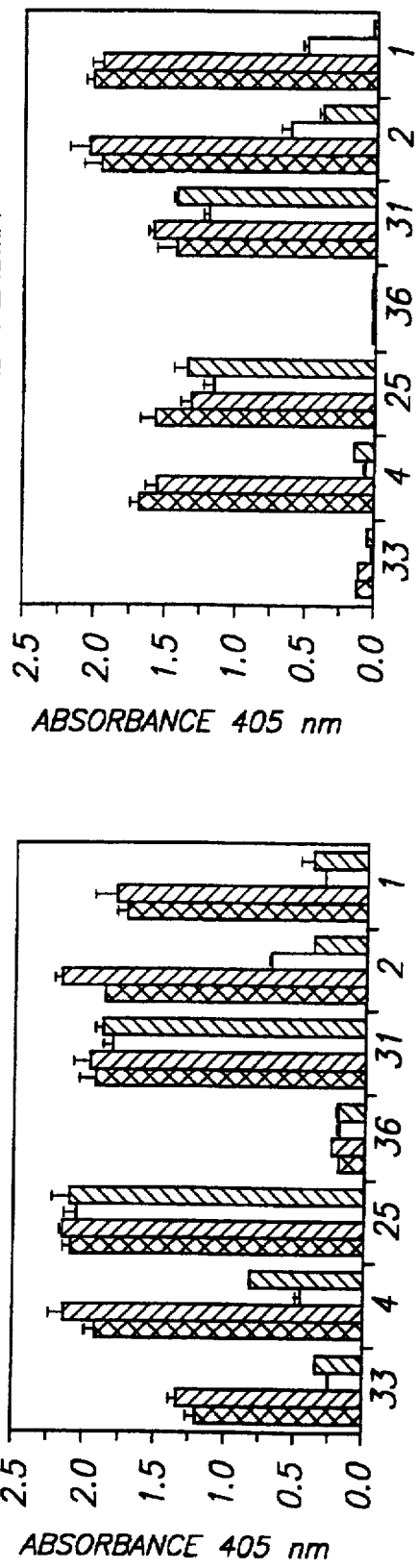
FIG. 11A  O PLASMA  HAPTEN-BSA CONJUGATE
FIG. 11B  AB PLASMA  HAPTEN-BSA CONJUGATE
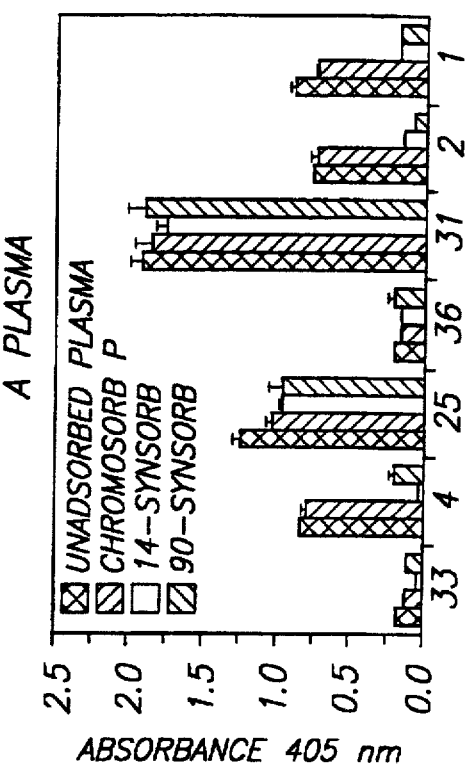
FIG. 11D  A PLASMA  HAPTEN-BSA CONJUGATE
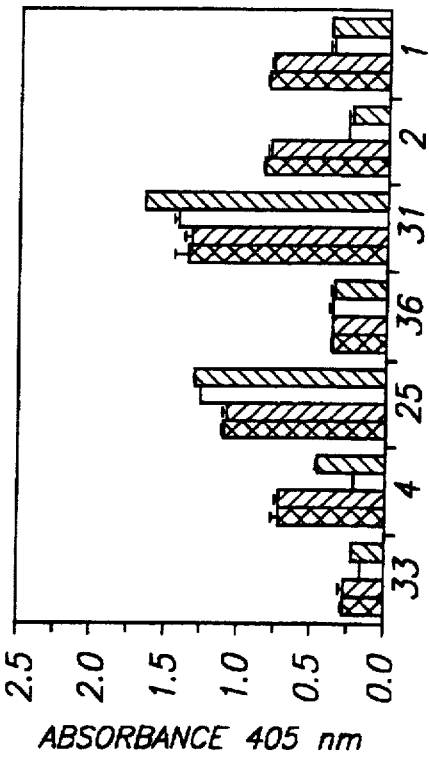
FIG. 11C  B PLASMA  HAPTEN-BSA CONJUGATE

METHODS AND COMPOSITIONS FOR ATTENUATING ANTIBODY-MEDIATED XENOGRAFT REJECTION IN HUMAN RECIPIENTS

This application is a divisional of application Ser. No. 07/933,466, filed Aug. 21, 1992 which, in turn, is a continuation-in-part of U.S. application Ser. No. 07/749,529 filed Aug. 23, 1991, now abandoned, which application is incorporated herein by reference in its entirety.

TECHNICAL FIELD

The present invention is in the general field of transplantation immunology and relates specifically to xenotransplantation and to compositions and methods for facilitating xenotransplantation in humans through inhibition and/or removal of preformed human antibodies to carbohydrate xenoantigens.

REFERENCES

The following references are cited in the application as superscript numbers at the relevant portion of the application.

1. Agashi, T.: Presentation at American Society for Artificial Internal Organs, 37th Annual Meeting in Chicago: Apr. 26, 1991.
2. Bannett, A. D., McAlack, R. P., Raja, R., Baquero, A., Morris, M.: Transplant. Proc. XIX:4543–4546, 1987.
3. Bensinger, W. I., Buckner, C. D., Thomas, E. D., Clift, R. A.: Transplantation. 33:427–429, 1982.
4. Chien, J. L., Li, S. C., Li, Y. T.: J. Lipid Res. 20:669–673, 1979.
5. Dubois, M., Gilles, K., Hamilton J. K., Rebers, P. A., Smith, F.: Anal. Chem. 28:350–356, 1956.
6. Egge, H., Kordowicz, M., Peter-Katalinic, J., Hanfland, P.: J. Biol. Chem. 260:4927–4935, 1985.
7. Eto, T., Ichikawa, Y., Nishimura, K., Ando, S., Yamakawa, T.: J. Biochem. (Tokyo) 64:205–213, 1968.
8. Galili, U., Clark, M. R., Shohet, S. B., Buehler, J., Macher, B. A.: Proc. Natl. Acad. Sci. 84: 1369–1373, 1987.
9. Galili, U., Macher, B. A., Buehler, J., Shohet, S. B.: J. Exp. Med. 162:573–582, 1985.
10. Galili, U., Shohet, S. B., Kobrin, E., Stults, C. L., Macher, B. A.: J. Biol. Chem. 263:17755–17762, 1988.
11. Holgersson, J., Cairns, T. D. H., Breimer, M. E., Taube, D., Welsh, K., Samuelsson, B. E.: Glycoconjugate J. 8:172, 1991.
12. Holgersson, J., Jovall, P. A., Samuelsson, B. E., Breamer, M. E.: J. Biochem. (Tokyo) 108:766, 1990.
13. Lemieux, R. U., Baker, D., Bundle, D.: U.S. Pat. No. 4,137,401, issued Jan. 30, 1979.
14. Lemieux, R. U., Baker, D., Bundle, D.: U.K. Patent No. 1544908, issued Aug. 29, 1979.
15. Lemieux, R. U., Bundle, D., Baker, D. A.: U.S. Pat. No. 4,238,473, issued Dec. 9, 1980.
16. Lemieux, R. U., Ratcliffe, R. M.: U.S. Pat. No. 4,362,720, issued Dec. 7, 1982.
17. Mazid, M. A.: European Patent Application No. 89311540.2 (Publication # 0 371 636 A2), filed Nov. 8, 1989.
18. Mazid, M. A.: U.S. Pat. No. 5,149,425.
19. Pinto, B. M., Bundle, D. R.: Carbohydr. Res. 124:313–318, 1983.
20. Platt, J. L., Lindman, B. J., Chen, H., Spitalnik, S. L., Bach, F. H.: Transplant. 50:817–822, 1990.
21. Rapp, H. J., Borsos, T.: J. Immunol. 96:913–919, 1966.
22. Stellner, K., Hakomori, S., Warner, G. A.: Biochem. Biophys. Res. Commun. 55:439–445, 1973.
23. Stults, C. L., Sweeley, C. C., Macher, B. A.: Methods in Enzymology 179:167–213, 1989.
24. Weetall, H. H.: Methods in Enzymology XLIV:140, 1976.
25. Cox, D. D., Metzner, E. K., Reist, E. J.: Carbohydr. Res. 62:245–252, 1978.
26. Dahmen, J., Torbjorn, F., Magnusson, G., Noori, G., Carlstrom, A.: Carbohydr. Res. 127:15–25, 1984.
27. Garegg, P. J., Oscarson, S.: Carbohydr. Res. 136:207–213, 1985.
28. Garegg, P. J., Oscarson, S.: Carbohydr. Res. 137:270–275, 1985.
29. Jacquinet, J., Duchet, D., Milat, M., Sinay, P.: J.C.S. Perkin I:326–330, 1981.
30. Koike, K., Sugimoto, M., Sato, S., Ito, Y., Nakahara, Y., Ogawa, T.: Carbohydr. Res. 163:189–208, 1987.
31. Schaubach, R., Hemberger, J., Kinzy, W.: Liebigs Ann. Chem. 607–614, 1991.
32. Laus, R., Ulrichs, K., Muller-Ruchholtz, W.: Int. Archs. Allergy Appl. Immun. 85:201–207, 1988.
33. Ratcliffe et al., U.S. Pat. No. 5,079,353, issued Jan. 7, 1992, for "Sialic Acid Glycosides, Antigens, Immunoadsorbents, and Methods for Their Preparation".
34. Okamoto et al., Tetrahedron, Vol. 46, No. 17, pp. 5835–5857 (1990).
35. Abbas et al., Proc. Japanese-German Symp. Berlin, pp. 20–21 (1988).
36. Paulsen, Angew. Chem. Int. Ed. Eng., 21:155–173 (1982).
37. Schmidt, Angew. Chem. Int. Ed. Eng., 25:212–235 (1986).
38. Fugedi et al., Glycoconj. J., 4:97–108 (1987).
39. Kameyama et al., Carbohydr. Res., 209:$C_1$–$C_4$ (1991).
40. Ekborg et al., Carbohydr. Res. 110:55–67 (1982).
41. Dahmen et al., Carbohydr. Res. 118:292–301 (1983).
42. Rana et al., Carbohydr. Res. 91:149–157 (1981).
43. Amvam-Zollo et al., Carbohydr. Res. 150:199–212 (1986).
44. Paulsen et al., Carbohydr. Res. 104:195–219 (1982).
45. Chernyak et al., Carbohydr. Res. 128:269–282 (1984).
46. Fernandez-Santana et al., J. Carbohydr. Chem. 8:531–537 (1989).
47. Lee et al., Carbohydr. Res., 37:193 et seq. (1974).
48. Ratcliffe et al., U.S. Pat. No. 5,344,870.

All publications and patent applications mentioned in this specification are indicative of the level of skill of those skilled in the art to which this invention pertains. All publications and patent applications are herein incorporated by reference in their entirety to the same extent as if each individual publication or patent application was specifically and individually indicated to be incorporated by reference in its entirety.

BACKGROUND

Over 15,000 organ transplants were performed in the U.S.A. in 1990. (Annual Report of the U.S. Scientific Registry for Organ Transplantation and the Organ Procurement and Transplantation Network. 1990.) The appropriate organs were taken from 6,000 donors, of whom fewer than 4,500 were cadaveric donors. The number of patients on the waiting list of the United Network of Organ Sharing in the U.S.A. at any one time approximates 23,000. Therefore, many potential recipients will be waiting for periods considerably in excess of one year for suitable organ transplants.

As the success of organ transplantation increases steadily, more and more patients are being referred for these procedures, and the shortage of suitable organs is becoming ever more acute. At the present time, kidney transplantation is associated with a 1-year graft survival of well over 90%, heart transplantation with a graft survival of over 80%, and liver and pancreas transplantation with graft survival rates approaching 80%.

Despite major efforts at educating the public and the medical profession with regard to the need for suitable donors, the gap between the demand and the availability of suitable organs is likely to increase. An answer to this problem would be the use of animal organs. Non-human primates have been considered for use as donors in this context.

However, these animals are in short supply worldwide, and, particularly with regard to the larger apes, are frequently endangered species. They are, therefore, not numerous enough to be considered in this role, and, furthermore, the numbers could not easily be increased even by widespread captive breeding programs. Other disadvantages include relatively small size, making them unsuitable as donors of organs for adult humans, and the risk of viral infection. There would also be vociferous public opposition to the use of these animals on a significant scale.

More distant mammalian species, such as the pig, would be very suitable in many regards. They grow to an appropriate size, breed easily, can be reared in specific pathogen free herds or even gnotobiotic (germ-free) conditions, and are already bred in large numbers specifically for the purpose of human consumption. Organ transplantation between widely disparate species, such as pig and man, however, is followed by antibody-mediated hyperacute rejection within minutes or hours, and this rejection cannot be inhibited or treated by the currently available immunosuppressive regimens. If the problem of antibody-mediated rejection could be overcome, then organ transplantation may no longer be restricted by the number of human donors that become available each year.

The benefits to society would be considerable. At present, one-third of those awaiting heart transplantation die before a suitable organ becomes available. If animal organs were used, patients would be able to undergo transplantation as soon as it was deemed necessary, and the operations could be performed electively under ideal conditions without the need for emergency procedures. In addition, many patients are today not accepted onto transplant waiting lists if they have borderline contraindications, as it is felt that the relatively few donor organs that become available must be used in ideal patients. If there were no limitation on the number of donor organs, then organ transplantation would certainly be offered to very many more candidates. Thus, compositions and methods which would facilitate xenotransplantation would be extremely useful.

There has been some success in facilitating non-xenotransplants between ABO-mismatched individuals. In non-human transplantation the extracorporeal removal of naturally occurring anti-A and/or anti-B antibodies using a method similar to those described in several patents (U.S. Pat. Nos. 4,137,401[13] and 4,238,473[15]; U.K. Patent 1544908[14]; U.S. Pat. No. 5,149,425[18]; European Patent Application No. 89311540.2[17]) has enabled successful transplantation of kidneys and bone marrow between ABO-mismatched individuals (Bannett et al. 1987[2], Bensinger et al. 1982[3]).

Anti-A, anti-B and other anti-carbohydrate antibodies have been involved in allogeneic transfusion reactions and acute rejection of skin grafts, and transplanted organs. It has therefore been hypothesized that antibodies to carbohydrate determinants may play a significant role in the acute rejection of xenografts. Some studies indicate that certain carbohydrate structures are targets for xenoantibodies (Laus et al. 1988[32], Platt et al. 1990[20], Holgersson et al. 1991[11]).

Numerous glycolipids have been purified from mammalian cells and many of these structures are reviewed in a paper by Stults and associates (1989)[23]. Linear B type 2-like glycosphingolipids have been purified from cells obtained from rabbit, cattle, and new world monkeys (Eto et al. 1968[7], Stellner et al. 1973[22], Chien et al. 1979[4], Egge et al. 1985[6] and Galili et al. 1987[8]).

Numerous specificities of anti-carbohydrate antibodies have been identified in plasma from humans. Galili and associates (1985)[9] have identified that anti-αGal(1-3)βGal antibodies constitute as much as 1% of circulating human IgG. This group purified antibodies from human AB sera using αGal(1-3)βGal(1-4)βGlcNAc (linear B type 2) bound to biocompatible solid supports. They found that these antibodies bound to pig endothelial cells (from the aorta), pig epithelial cells (from the lens of the eye) and many other tissues from non-primate mammals and new world monkeys, but not to tissues from healthy old world monkeys, apes or man (Galili et al. 1988[10]).

In non-xenogeneic transplants, the neutralization or removal of anticarbohydrate antibodies utilizing A and B blood group trisaccharides covalently attached to a solid support in the form of an immunoadsorbent for the extracorporeal depletion of human anti-A and anti-B antibodies has been shown to facilitate kidney and bone marrow transplantation across the ABO blood group barrier (Bannett et al. 1987[2], Bensinger et al. 1982[3] and Agashi 1991[1]). This approach is currently in clinical trials. An injectable form of the A and B blood group trisaccharides for the in situ neutralization of anti-A and anti-B antibodies is currently in preclinical development. In studies of xenospecific antibody activity, utilization of other oligosaccharides covalently attached to a solid support was previously reported as not being particularly successful for removal of anticarbohydrate antibodies (Laus et al.[32])

DISCLOSURE OF THE INVENTION

The invention encompasses two techniques for facilitating transplantation of xenogeneic cells, tissues, or organs into humans. One technique involves extracorporeal removal of xenoantibodies from the recipient's blood. The other involves inhibiting xenoantibodies in vivo. The invention also encompasses compositions that are used in or result from these methods.

Accordingly, one aspect of the invention is a method for attenuating antibody-mediated xenograft rejection in a human recipient of a xenograft comprising: identifying one or more xenoantigens, attaching the xenoantigen(s) to a biocompatible solid support, withdrawing antibody-containing body fluid from the recipient, removing preformed antibodies to at least one carbohydrate antigen of said xenograft that is involved in the rejection from the withdrawn body fluid by extracorporeal perfusion of the body fluid over a biocompatible solid support to which the antigen(s) is bound through a compatible linker arm, and reintroducing the perfused body fluid into the recipient.

Another aspect of the invention is a method for attenuating antibody-mediated xenograft rejection in a human recipient of a xenograft comprising identifying at least one carbohydrate xenoantigen to preformed antibodies, and parenterally administering at least one carbohydrate xenoantigen capable of binding one or more antibodies that is involved in the rejection to the recipient in an mount sufficient to inhibit the recipient's antibodies to the antigen.

A further aspect of the invention is a composition useful for attenuating antibody-mediated xenograft rejection in a human recipient of a xenograft comprising an injectable formulation of at least one carbohydrate xenoantigen.

Yet another aspect of the invention is an immunoadsorbent composition useful for removing xenoantibodies from the blood of a human recipient of a xenograft to attenuate the rejection of the xenograft by the recipient comprising a biocompatible solid support having at least one identified xenoantigen attached thereto through a compatible linker arm.

Still another aspect of the invention is human blood or plasma useful for infusing into a human recipient of a xenograft to attenuate rejection of said xenograft, the blood or plasma being depleted of preformed antibodies to at least one identified xenoantigen.

BRIEF DESCRIPTION OF THE DRAWINGS

FIGS. 1A–1H illustrate carbohydrate structures used to study the binding of human antibodies eluted from pig heart, pig kidney and/or pig red cell stroma.

FIGS. 11A–11D illustrate removal of antibodies when human plasma (O, A, B and AB) were preadsorbed with some matrix-bound carbohydrate antigens as detected by ELISA.

MODES FOR CARRYING OUT THE INVENTION

A. Definitions

Figure 1A:
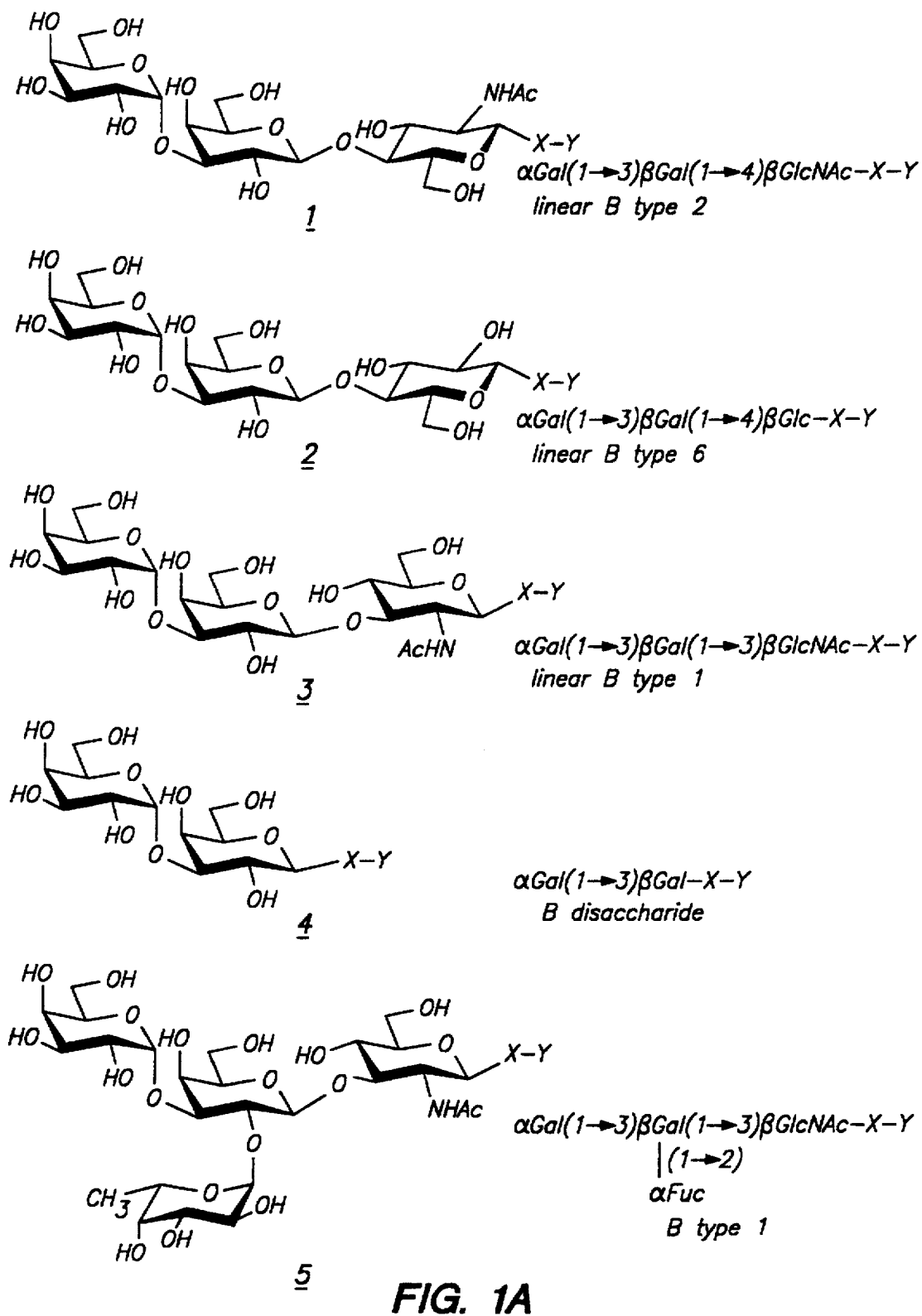
Figure 1D:
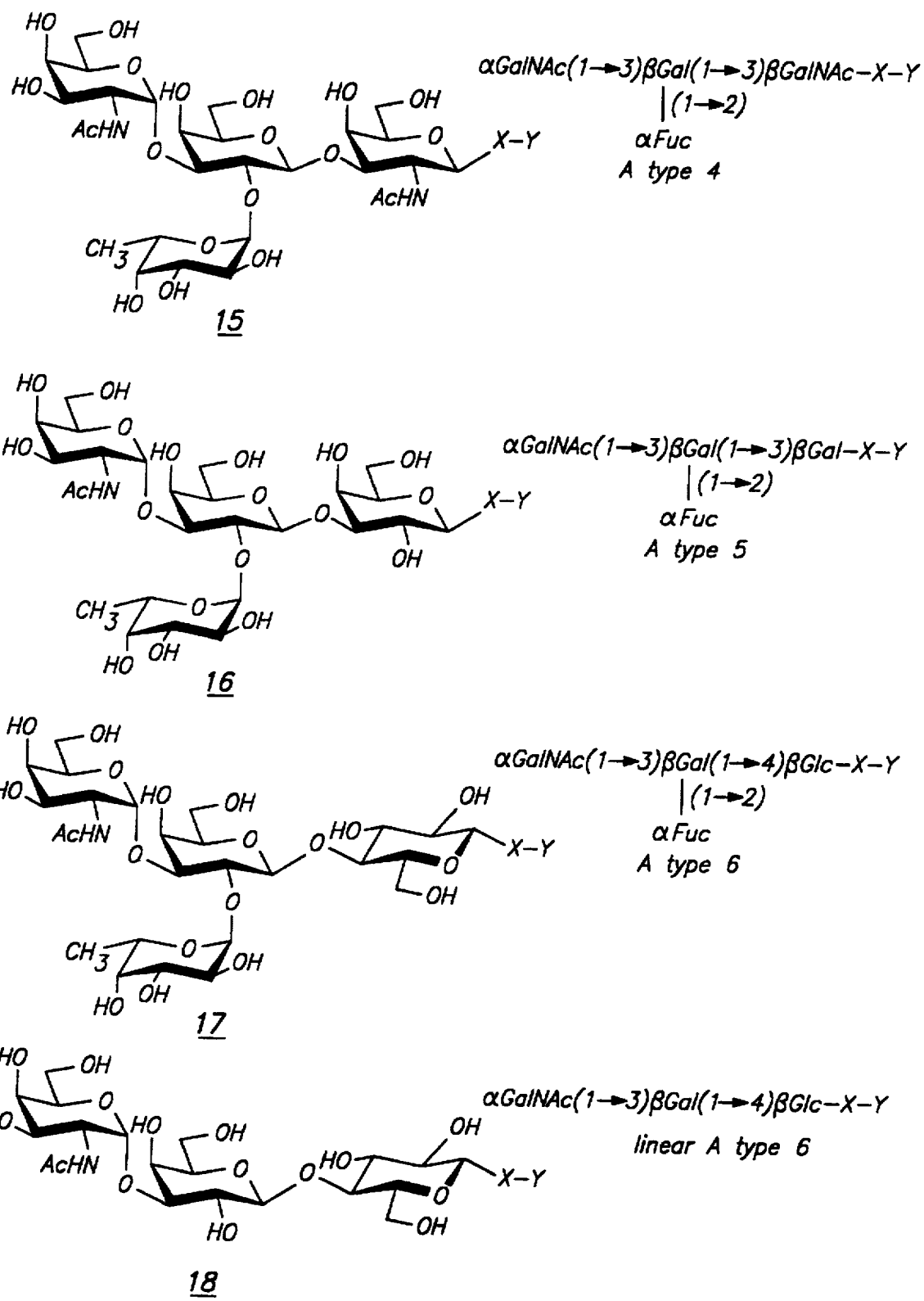
Figure 1E:
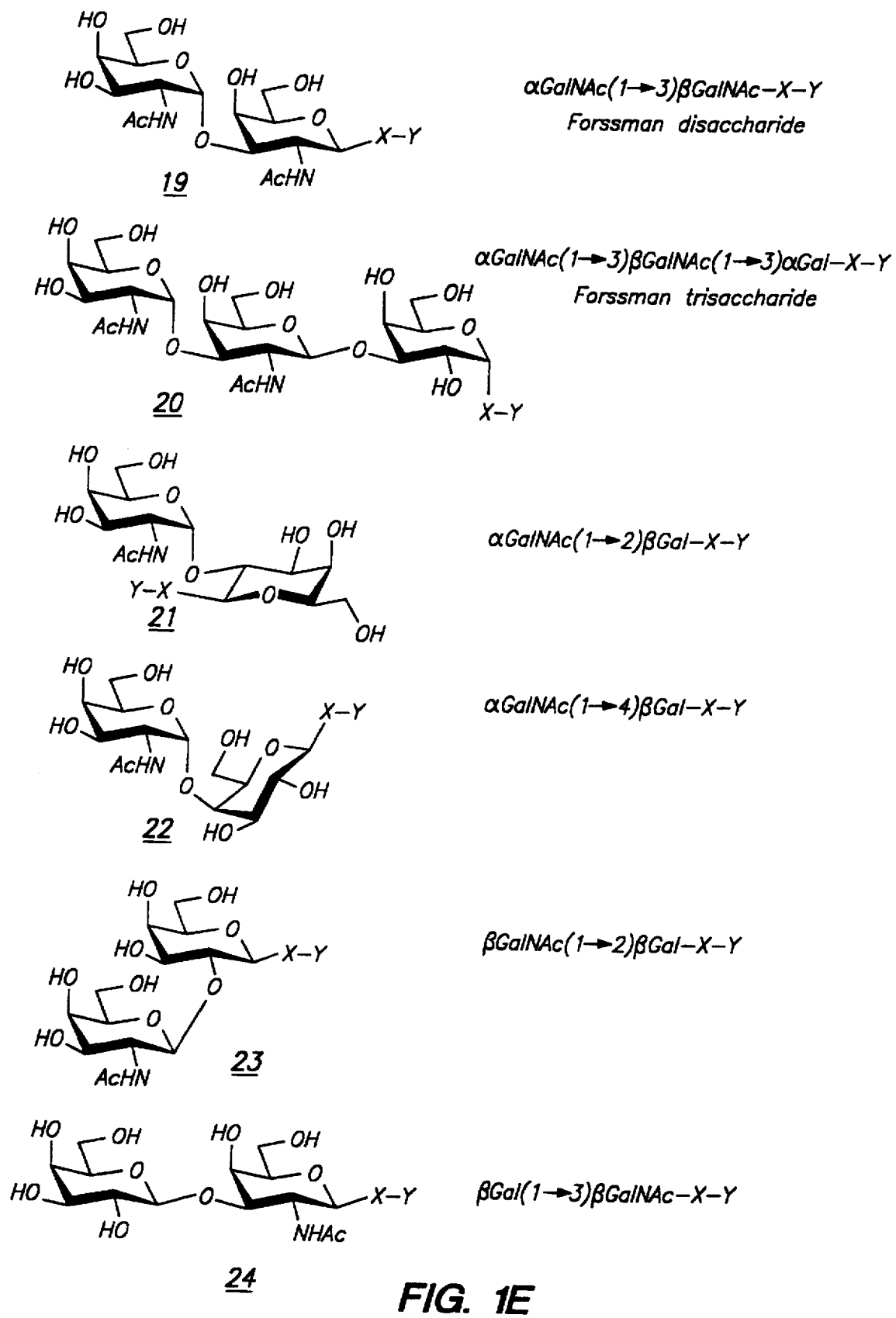
Figure 1G:
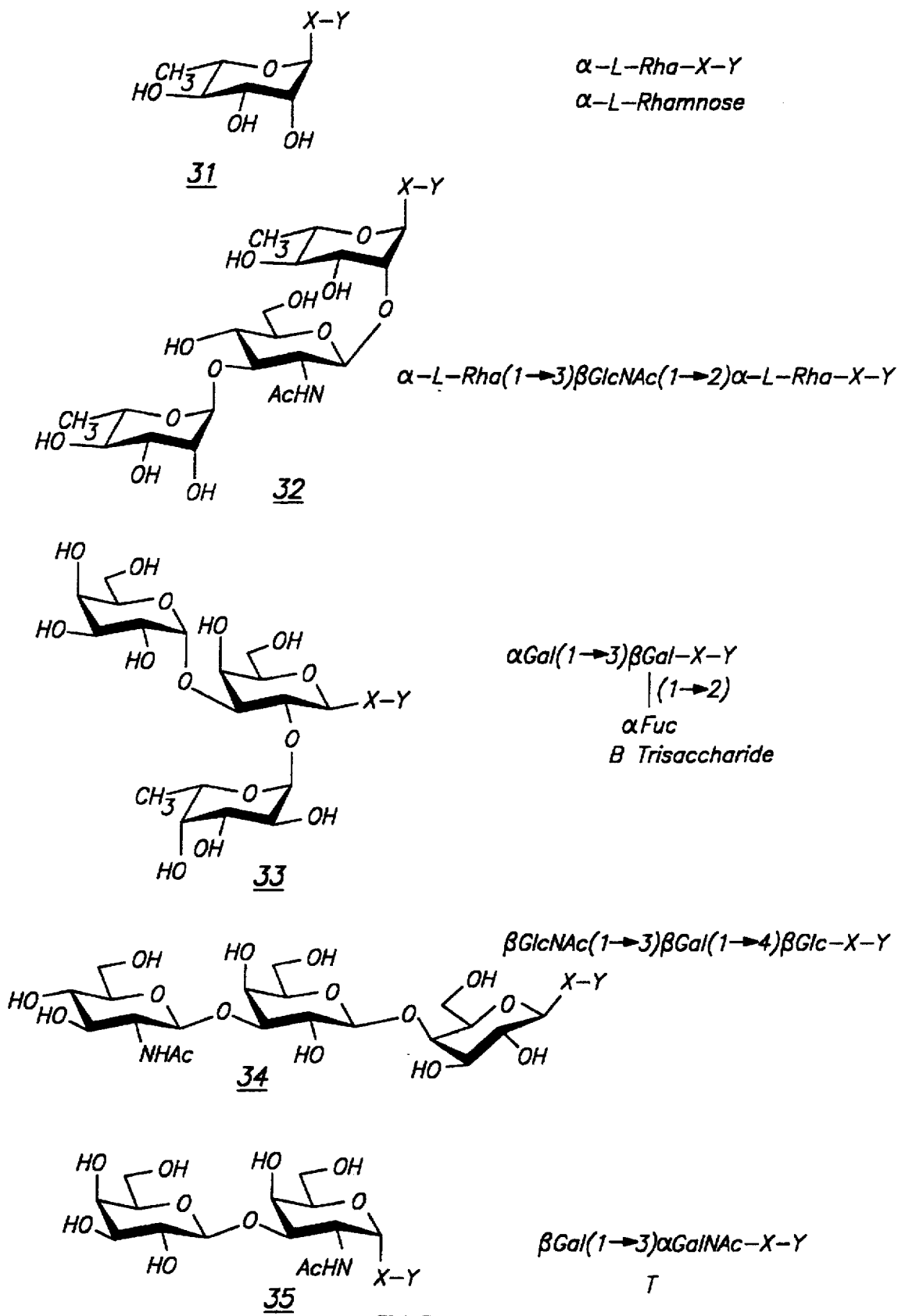

As used herein the following terms have the following meanings:

Xenograft: a cell, tissue, or organ graft of a nonhuman mammalian species that normally gives rise to a rejection response in a human recipient.

Rejection: an immune response with humoral and/or cellular components directed against a xenograft.

Attenuation: a reduction or elimination of either or both components of a rejection response.

Antibody-mediated: an immune response that directly or indirectly results from antigen-antibody interaction.

Inhibit: a reduction or elimination of the ability of an antibody to induce a rejection response.

Xenoantigen: a carbohydrate antigen of a xenograft, particularly one that is involved in a rejection response or an antigen that cross-reacts with an antibody capable of binding to a carbohydrate antigen of a xenograft.

Xenoantibodies: pre-formed (existing) human antibodies that recognize and bind xenoantigens as pan of the rejection response.

Biocompatible: chemical inertness with respect to human antibody-containing body fluids.

Blood: whole blood, plasma or serum.

Compatible linker arm: a moiety which serves to space the carbohydrate antigen from the biocompatible solid support and which is bifunctional wherein one functional group is capable of binding to a reciprocal functional group of the support and the other functional group is capable of binding to a reciprocal functional group of the carbohydrate antigen.

B. Extracorporeal Removal of Xenoantibodies from Body Fluids

As indicated, one aspect of this invention involves the steps of identifying one or more xenoantigens, attaching the xenoantigen(s) to a biocompatible solid support, withdrawing antibody-containing body fluid from a human xenograft recipient, removing preformed antibodies to one or more xenoantigens from the fluid via affinity chromatography, and reintroducing the xenoantibody-depleted body fluid into the recipient.

While this technique may be applied to any antibody-containing body fluid, it will usually be applied to blood. The blood is withdrawn by conventional techniques and an anticoagulant (e.g., heparin, citrate) is typically added to it to prevent coagulation. If desired, cells may be removed from the blood before it is subjected to xenoantibody depletion.

Xenoantibody depletion is achieved by perfusing the blood over a solid support having one or more xenoantigens bound to it. Xenoantigens may be identified by isolating xenoantibodies from human blood by perfusing the blood over xenograft material, removing bound antibodies from the xenograft, and using those antibodies to screen candidate carbohydrates, such as by a suitable immunoassay. Examples of such xenoantigens are the carbohydrates listed in Table 1, infra, and shown in FIG. 1A to 1H.

Chemical methods for the synthesis of carbohydrate xenoantigens can be accomplished by methods known in the art. These materials are generally assembled using suitably protected individual monosaccharides including the desirable glucose, N-acetylglucosamine, galactose, N-acetylgalactosamine, fucose, and rhamnose or lactose intermediate.

The specific methods employed are generally adapted and optimized for each individual structure to be synthesized. In general, the chemical synthesis of all or part of the oligosaccharide glycosides first involves formation of a glycosidic linkage on the anomeric carbon atom of the reducing sugar or monosaccharide. Specifically, an appropriately protected form of a naturally occurring or of a chemically modified saccharide structure (the glycosyl donor) is selectively modified at the anomeric center of the reducing unit so as to introduce a leaving group comprising halides, trichloroacetimidate, acetyl, thioglycoside, etc. The donor is then reacted under catalytic conditions well known in the art with an aglycon or an appropriate form of a carbohydrate acceptor which possesses one free hydroxyl group at the position where the glycosidic linkage is to be established. A large variety of aglycon moieties are known in the an and can be attached with the proper configuration to the anomeric center of the reducing unit.

Appropriate use of compatible blocking groups, well known in the an of carbohydrate synthesis, will allow selective modification of the synthesized structures or the further attachment of additional sugar units or sugar blocks to the acceptor structures.

After formation of the glycosidic linkage, the saccharide glycoside can be used to effect coupling of additional saccharide unit(s) or chemically modified at selected positions or, after conventional deprotection, used in an enzymatic synthesis. In general, chemical coupling of a naturally occurring or chemically modified saccharide unit to the saccharide glycoside is accomplished by employing established chemistry well documented in the literature. See, for example, Okamoto et al.[34], Ratcliffe et al.[33], Abbas et al.[35], Paulson[36], Schmidt[37], Fugedi et al.[38], and Kameyama et al.[39], U.S. Pat. Nos. 4,137,401[13], 4,238,473[15], and 4,362,720[16] and in Dahmen et al.[26], Schaubach et al.[31], Garegg et al.[27,28], Jacquinet et al.[29], Cox et al.[25], and Koike et al.[30]

In the monosaccharide and oligosaccharide glycosides shown in FIGS. 1A to 1H, X represents oxygen, sulfur, —NH— or a covalent bond, and Y represents hydrogen or an aglycon group (i.e., that component of a glycoside which is not a sugar). In most instances Y represents a radical of the general formula —A—Z wherein A represents a bond, an alkylene group of from 2 to 10 carbons, or —(CH$_2$—CR$_1$—G)$_n$— wherein n is an integer equal to 1 to 5 inclusive; R$_1$ is selected from the group consisting of hydrogen, methyl and ethyl; and G is selected from the group consisting of hydrogen, oxygen, sulfur, nitrogen, phenyl, and phenyl substituted with 1 to 3 substituents selected from the group consisting of amine, hydroxyl, halo, and alkyl of from 1 to 4 carbon atoms, and Z is selected from the group consisting of hydrogen, methyl and when G is not oxygen, sulfur or nitrogen and A is not a bond, then Z is also selected from the group consisting of OH, SH, —NH$_2$, NHR$_2$, —C(O)OR$_2$, —C(O)NH$_2$, —C(O)NH—NHR$_2$, —C(O)NHR$_2$ and —C(O)N(R$_2$)$_2$ wherein each R$_2$ is independently hydrogen or alkyl of from 1 to 4 carbon atoms.

Preferably X represents —O— and Y represents —A—Z wherein A is alkylene of 2 to 10 carbon atoms and Z is selected from the group consisting of —C(O)OR$_2$, —C(O)NH$_2$, and —C(O)NHR$_2$ and R$_2$ is hydrogen or alkyl of from 1 to 4 carbon atoms.

Particularly preferred carbohydrates from among those shown in FIGS. 1A to 1H are carbohydrates of formulas 1, 2, 3, 4, 13, 25, 26, 31, and 32 wherein X is —O— and Y is —A—Z where A is alkylene of 2 to 10 carbon atoms and Z is selected from the group consisting of —C(O)OR$_2$, —C(O)NH$_2$ and —C(O)NHR$_2$ where R$_2$ is hydrogen or alkyl of from 1 to 4 carbon atoms.

The solid supports to which the xenoantigens are bound may be in the form of a continuous large surface or in the form of particles. A large variety of biocompatible solid support materials are known in the art. Examples thereof are silica, synthetic silicates such as porous glass, biogenic silicates such as diatomaceous earth, silicate-containing minerals such as kaolinite, and synthetic polymers such as polystyrene, polypropylene, and polysaccharides. Preferred supports are described in U.S. Pat. No. 5,149,425[18], filed 9 Nov. 1988, the disclosure of which is incorporated herein by reference.

The xenoantigen(s) is covalently bound or noncovalently (passively) adsorbed onto the solid support. The covalent bonding may be via reaction between functional groups on the support and the compatible linker arm of the xenoantigen. It has unexpectedly been found that attachment of the carbohydrate antigen to the biocompatible solid support through a compatible linking arm gives effective removal of anticarbohydrate antibodies. Linking moieties that are used in indirect bonding are preferably organic bifunctional molecules of appropriate length (at least one carbon atom) which serve simply to distance the antigen from the surface of the solid support. The particular linking arm is not critical.

Numerous aglycon linking arms are known in the art. For example, a linking arm comprising a para-nitrophenyl group (i.e., —YR=—OC$_6$H$_4$pNO$_2$) has been disclosed by Ekborg et al.[40] At the appropriate time during synthesis, the nitro group is reduced to an amino group which can be protected as N-trifluoroacetamido. Prior to coupling to a support, the trifluoroacetamido group is removed thereby unmasking the amino group.

A linking arm containing sulfur is disclosed by Dahmen et al.[41] Specifically, the linking arm is derived from a 2-bromoethyl group which, in a substitution reaction with thionucleophiles, has been shown to lead to linking arms possessing a variety of terminal functional groups such as —OCH$_2$CH$_2$SCH$_2$CO$_2$CH$_3$ and —OCH$_2$CH$_2$SC$_6$H$_4$—pNH$_2$.

Rana et al.[42] discloses a 6-trifluoroacetamido-hexyl linking arm (—O—(CH$_2$)$_6$—NHCOCF$_3$) in which the trifluoroacetamido protecting group can be removed unmasking the primary amino group used for coupling.

Other exemplification of known linking arms include the 7-methoxycarbonyl-3,6,dioxaheptyl linking arm[43] (—OCH$_2$—CH$_2$)$_2$OCH$_2$CO$_2$CH$_3$); the 2-(4-methoxycarbonylbutancarboxamido)ethyl[44] (—OCH$_2$CH$_2$NHC(O)(CH$_2$)$_4$CO$_2$CH$_3$); the allyl linking arm[45] (—OCH$_2$CH=CH$_2$) which, by radical co-polymerization with an appropriate monomer, leads to copolymers; other allyl linking arms[46] are known [—O(CH$_2$CH$_2$O)$_2$CH$_2$CH=CH$_2$]. Additionally, allyl linking arms can be derivatized in the presence of 2-aminoethanethiol[47] to provide for a linking arm —OCH$_2$CH$_2$CH$_2$SCH$_2$CH$_2$NH$_2$. Other suitable linking arms are disclosed in U.S. Pat. Nos. 4,137,401[13], 4,238,473[15], and 4,362,720[16] and in Dahmen et al.[26] and Garegg et al.[27].

Additionally, as shown by Ratcliffe et al.[48], the R group can be an additional saccharide or an oligosaccharide containing a linking arm at the reducing sugar terminus.

Preferably, the aglycon moiety is a hydrophobic group and most preferably, the aglycon moiety is a hydrophobic group selected from the group consisting of —(CH$_2$)$_8$ COOCH$_3$, —(CH$_2$)$_5$OCH$_2$CH=CH$_2$ and —(CH$_2$)$_8$CH$_2$OH.

The functional linking arm of the carbohydrate antigen is then used to attach the antigen to a biocompatible solid support. Such attachment is well known in the art and is disclosed, for example, by Venot et al., U.S. Ser. No. 07/887,746, (refiled as continuation application Ser. No. 08/326,745) which is incorporated herein by reference in its entirety.

Solid supports having combinations of two or more xenoantigens bound thereto may be used to remove xenoantibodies of different specificity from the blood or plasma. Alternatively, the blood or plasma may be passed successively over a series of solid supports each of which has one or more different xenoantigens bound thereto to remove xenoantibodies of different specificity. Accordingly, based on the results of the examples it may be desirable to use combinations of one or more linear B type carbohydrate xenoantigens with another type of carbohydrate antigen (e.g., an A type antigen, a Forssman type antigen, a Rhamnose antigen, or a glucosaminide type antigen (see FIGS. 1A to 1H)). In the case of porcine xenografts, combinations of at least linear B type 2 and linear B type 6 antigens may be preferred. Such combinations of antigens may also be employed in the xenoantibody inhibition procedure described below.

The blood will be contacted with the solid support under conditions that promote binding between the xenoantigens bound to the support and complementary xenoantibodies present in the blood or plasma. A preferred apparatus and technique for carrying out extracorporeal hemoperfusion is described in said U.S. Pat. No. 5,149,425[18]. Contact temperatures in the range of 35° C. to 40° C. are preferably used. The contact time will typically be in the range of 1 to 6 hr. The unbound portion of the blood or plasma (i.e., xenoantibody-depleted blood or plasma) is then collected for reintroduction into the patient or it can be reintroduced directly on a continuous basis. The removal of xenoantibodies from the recipient's blood is carried out prior to transplantation (it is typically repeated daily up to 8 times before transplantation) so that the xenograft is introduced in the substantial absence of the xenoantibodies or at a time when the xenoantibodies are present at relatively low titers. The recipient's xenoantibody titer may be monitored by immunoassay. Insertion of the graft under such conditions lessens the likelihood of antibody-mediated hyperacute rejection (even though antibody titers may subsequently increase) and enhances graft survival. This phenomenon is variously termed "accommodation," "adaptation," or "anergy." Xenoantibody removal may be continued after transplantation if necessary.

Conventional pharmacologic immunosuppression regimes employing nonspecific immunosuppressive agents such as cyclosporine, methylprednisolone, and azathioprine may be employed in conjunction with either or both of the invention methods.

C. Inhibition of Xenoantibodies In Vivo

As indicated, this technique involves parenterally introducing one or more identified xenoantigens into the xenograft recipient. Once introduced into the circulation, these xenoantigens will bind to pre-formed xenoantibodies to neutralize the activity of those xenoantibodies.

The same xenoantigens that are used in the xenoantibody removal technique may be used in the inhibition technique. One or more of these xenoantigens or pharmaceutically acceptable derivatives thereof (e.g., esters) is formulated as an injectable in a conventional pharmaceutically acceptable injectable vehicle (e.g., water for injection). Formulation typically involves mixing the antigen(s) with the vehicle, depyrogenating the mix by ultrafiltration, and sterile filtering the depyrogenated mix. The mix may be lyophilized for storage and reconstituted in sterile vehicle if desired.

The injectable formulation may be administered by intermittent bolus injection or by continuous intravenous infusion. The administration will typically be initiated shortly before revascularization of the xenograft and continued for a varying period of time following transplantation. The particular dosing and administration regimen may vary depending upon the type of transplant, the age, weight, and medical history of the recipient and donor, and the pharmacokinetics of the xenoantigen(s). Typically, the xenoantigens will be administered continuously at doses ranging between about 100 mg/hr and 1000 mg/hr for 1 to 20 days. Concomitant pharmacologic immunosuppression is preferred. Extracorporeal removal of xenoantibodies as described previously may be used in combination with parenteral administration of xenoantigens.

D. Examples

The following examples demonstrate that a wide range of human anti-nonhuman mammalian antibodies are directed at carbohydrate antigens on the cells of a porcine xenograft, that some of these antibodies are cytotoxic (hemolytic) for cells of the xenograft and that application of monosaccharides and/or oligosaccharides, either alone or in combination, substantially neutralize these cytolytic antibodies.

In these examples, unless otherwise defined below, the abbreviations employed have generally accepted meaning:
ELISA=Enzyme linked immunosorbent assay
BSA=Bovine serum albumin
DMF=dimethylformamide
PBS=Phosphate buffered saline=7.8 mM Na$_2$HPO$_4$, 2.2 mM KH$_2$PO$_4$, 154 mM NaCl and 15 mM NAN$_3$, pH 7.1 to 7.3
Gal=Galactose
Glc=Glucose
Man=Mannose
GlcNAc=N-acetylglucosamine
GalNAc=N-acetylgalactosamine
Fuc=Fucose
Rha=Rhamnose
FBS=fetal bovine serum
rpm=revolutions per minute
cpm=counts per minute
U=unadsorbed
P=adsorbed with Chromosorb P
LacNAc=βGal(1-4)βGlcNAc-R, R=—(CH$_2$)$_8$—CONH—SYNSORB in Example 3 or R=—(CH$_2$)$_8$—COOCH$_3$ in Example 4.
SYNSORB=synthetic carbohydrate structures bound to Chromosrb P through a —(CH$_2$)$_8$—CONH— linking arm.

Reference numbers in FIGS. 4A–12D denote formulas of compounds as set forth in FIGS. 1A to 1H.

These examples are not intended to limit the scope of the invention in any manner.

EXAMPLE 1

Identification of Carbohydrate Compounds Which Bind Human Anti-mammalian Antibodies a) Isolation of human "anti-pig" antibodies Organs from two populations of pigs were used to purify human anti-pig antibodies. The pig strains were Poland China and Yorkshire. Antibody preparations were obtained by perfusing 100–200 ml of human plasma (O or AB) through pig hearts, pig kidneys or through a column containing solid support coated with pig red cell stroma. After washing the tissues thoroughly with 0.15M NaCl, the retained antibodies were eluted from the tissue or column using 200 ml of 3M NaSCN. The antibodies were concentrated, and then the protein content determined.

b) Carbohydrate antigens

Carbohydrate antigens were made by covalent binding of the synthetic oligosaccharides with an aliphatic linking arm $(CH_2)_8COOCH_3$ to BSA as described by Pinto and Bundle (1983)[19] and/or Lemieux, Bundle, Baker (U.S. Pat. No. 4,137,401)[13] (ten to twenty haptens per molecule of BSA). Example 5, infra, describes this procedure as applied to carbohydrate 2 of FIG. 1A. Structures and trivial names of some of the monosaccharides and oligosaccharides used are included in FIGS. 1A to 1H. The use of synthetic carbohydrate structures to detect antibody binding has been previously described in U.S. Pat. No. 4,137,401[13].

c) Enzyme linked immunosorbent assay (ELISA)

The technology used for the ELISA assay for detecting anti-carbohydrate antibodies is a combination of the work from numerous groups. Wells in 96 microtitration plates (Flow Laboratories, Inc., McLean Va., U.S.A.) were coated by incubation at room temperature for 16 hours with 2 µg of BSA-glycoconjugates or BSA per well (20 µg BSA-conjugate/ml diluted in PBS). The coating solutions were removed and 200 µl/well of PBS containing 5% BSA was added. After a 4 hours incubation (22° C.), the wells were washed twice with PBS, then once with $H_2O$. The plates were inverted, allowed to dry, and stored at room temperature.

Immediately before testing, 200 µl of PBS containing 1% BSA (1% BSA/PBS) was added to each of the wells and left to stand for 10 to 20 minutes at ambient temperature. The human anti-pig preparations were diluted to between 15 to 70 µg of eluted protein per ml of 1% BSA/PBS. The BSA/PBS was removed and 100 µl of diluted anti-pig preparation was added to the appropriate wells, then incubated at 4° C. for 16 hours. The antibody preparations were removed and the wells were washed 4 times with PBS (200 µl/wash). Alkaline phosphatase-conjugated reagents (anti-human polyvalent ($\alpha$, $\gamma$ and µ chain specific), anti-human IgG ($\gamma$ chain specific) and anti-human IgM (µ chain specific)) from Sigma Chemical Company (St. Louis, Mo., U.S.A.) were each diluted 1/500 in 1% BSA/PBS. One hundred µl of this mixture was added to each well. After 2 hours, wells were washed four times with PBS, then 100 µl/well of 1.0 mg of p-nitrophenyl phosphate/ml of 1M diethanolamine-HCl (pH 9.8) containing 1% BSA and 500 µM $MgCl_2$ was added. After 1 hour, optical densities at 405 nm (O.D.) were measured using a Microplate Autoreader (Model EL 309, BIO-TEK Instruments, Winooski, Vt., U.S.A.). The O.D. results for BSA-coated wells were subtracted from the results for the glycoconjugate-BSA-coated wells for each preparation. The assays were performed in duplicate. The anti-human immunoglobulin conjugated to alkaline phosphatase did not bind significantly to any of the structures tested. The results are reported in Table 1.

TABLE 1

Human Antibodies Eluted from Pig Tissues Binding to Carbohydrate Antigens

| Reference Number (FIGS. 1A to 1H) | Optical Density (405 nm) | | | | | | | | | | | |
|---|---|---|---|---|---|---|---|---|---|---|---|---|
| | Human Anti-Pig Kidney | | | | | | | | Human Anti-Pig Heart | | | |
| | 5 A° | 5 B^AB | 6 A° | 6 B^AB | 7 A^AB | 7 B° | 8 A° | 9 B^AB | 5^AB | 6° | 7^AB | 9° |
| 1 | 2.0 | 1.7 | 1.8 | >2.0 | 0.8 | 1.8 | 1.2 | >2.0 | 0.9 | 0.2 | 1.2 | 0.8 |
| 2 | 1.9 | 1.3 | >2.0 | >2.0 | 0.8 | 1.8 | 1.2 | >2.0 | 1.0 | 0.3 | 1.2 | 0.8 |
| 4 | 1.6 | 1.7 | >2.0 | >2.0 | 0.6 | 1.6 | 0.9 | 0.6 | 0.8 | 0.2 | 0.8 | 0.7 |
| 7 | 1.1 | 0.0 | 1.4 | 0.0 | 0.0 | 1.3 | 0.2 | 0.0 | 0.0 | 0.2 | 0.1 | 0.3 |
| 8 | 1.1 | 0.0 | 1.7 | 0.0 | 0.0 | 1.0 | 0.2 | 0.0 | 0.0 | 0.1 | 0.1 | 1.2 |
| 10 | 0.6 | 0.0 | 0.8 | 0.0 | 0.4 | 0.5 | 0.0 | 0.1 | 0.8 | 0.1 | 0.6 | 0.6 |
| 11 | 0.2 | 0.1 | 0.3 | 0.0 | 0.1 | 0.0 | 0.0 | 0.0 | 0.1 | 0.1 | 0.3 | 0.8 |
| 12 | 0.2 | 0.2 | 1.9 | 0.3 | 0.1 | 1.1 | 0.1 | 0.0 | 1.1 | 0.8 | 0.5 | 0.3 |
| 13 | 0.6 | 0.0 | 0.5 | 0.0 | 0.1 | 0.9 | 0.0 | 0.0 | 0.0 | 0.2 | 0.0 | 0.3 |
| 15 | 0.2 | 0.0 | 0.7 | 0.0 | 0.0 | 1.9 | 0.0 | 0.0 | 0.0 | 0.3 | 0.1 | 0.6 |
| 16 | 0.1 | 0.0 | 0.6 | 0.0 | 0.1 | 1.6 | 0.1 | 0.0 | 0.1 | 0.3 | 0.1 | 0.5 |
| 17 | 1.0 | 0.0 | 0.3 | 0.0 | 0.0 | 1.3 | 0.0 | 0.0 | 0.0 | 0.6 | 0.1 | 0.4 |
| 18 | 0.2 | 0.1 | 1.1 | 0.1 | 0.2 | 0.9 | 0.1 | 0.0 | 0.9 | 0.4 | 0.4 | 0.4 |
| 19 | 1.2 | 0.4 | 0.4 | 0.1 | 0.4 | 1.2 | 0.1 | 0.1 | 0.7 | 1.5 | 0.7 | 0.2 |
| 20 | 0.8 | 0.4 | 0.7 | 0.4 | 0.3 | 1.9 | 0.1 | 0.0 | 0.6 | 1.6 | 0.8 | 0.4 |
| 21 | 0.1 | 0.4 | 0.1 | 0.8 | 0.3 | 0.8 | 0.1 | 0.2 | 0.7 | 0.6 | 1.8 | 0.4 |
| 22 | 0.1 | 0.0 | 1.1 | 0.0 | 0.1 | 0.1 | 0.0 | 0.0 | 0.5 | 0.1 | 0.3 | 0.5 |
| 23 | 0.1 | 0.6 | 0.3 | 0.2 | 0.9 | 0.2 | 0.0 | 0.3 | 0.6 | 0.5 | 0.9 | 0.4 |
| 24 | 0.2 | 0.0 | 0.2 | 0.0 | 0.7 | 0.1 | 0.0 | 0.1 | 0.2 | 0.3 | 0.4 | >2.0 |
| 25 | 0.5 | 0.7 | 0.4 | 1.0 | 1.1 | 0.5 | 0.1 | 0.1 | 2.0 | 0.4 | >2.0 | 1.5 |
| 26 | 0.4 | 0.3 | 0.2 | 0.4 | 0.9 | 0.1 | 0.0 | 0.1 | 0.5 | 0.2 | >2.0 | 1.7 |
| 27 | 0.1 | 0.1 | 0.2 | 0.2 | 0.1 | 0.6 | 0.0 | 0.1 | 0.3 | 0.1 | 1.1 | 0.5 |
| 28 | 0.2 | 0.4 | 0.7 | 0.3 | 1.0 | 0.3 | 0.0 | 0.1 | 0.4 | 0.1 | 1.2 | 1.8 |
| 29 | 0.1 | 0.4 | 0.2 | 0.1 | 0.5 | 0.2 | 0.0 | 0.1 | 1.2 | 0.2 | 0.7 | 0.6 |
| 30 | 0.4 | 0.1 | 0.2 | 0.1 | 0.6 | 0.1 | 0.0 | 0.1 | 0.1 | 0.1 | >2.0 | 0.4 |
| 31 | 0.2 | 0.0 | 0.3 | 0.5 | 1.7 | 0.1 | 0.0 | 0.1 | 0.7 | 0.4 | >2.0 | 0.6 |
| 32 | 1.4 | 0.8 | 0.1 | 0.3 | 1.9 | 0.8 | 0.1 | 0.1 | 1.0 | 0.3 | 1.6 | 1.1 |

°Human o plasma adsorbed onto tissue
^AB Human plasma adsorbed onto tissue

Numerous carbohydrate structures bound antibodies eluted from pig heart, pig kidney and/or pig red cell stroma. Some of these structures are included in Table 1. As shown in Table 1, B-like carbohydrate molecules (especially linear B type 2 and linear B type 6) exhibited the most reactivity for the majority of samples tested, including anti-pig heart and anti-pig kidney.

For individual eluted antibody preparations other carbohydrate antigens bound antibodies, including A or A-like carbohydrates (namely A disaccharide, A trisaccharide, a variety of A tetrasaccharides and linear A type 6); Forssman disaccharide and Forssman trisaccharide; α-L-Rhamnose and Rhamnose-containing structures; N-acetyl-β-D-glucosaminide (βGlcNAc) and βGlcNAc-containing structures (Table 1). However, not all of these antigens bound significant levels of antibody for all preparations.

The populations of anti-carbohydrate antibodies varied depending on the particular tissue and the individual serum adsorbed, but anti-linear B type 2, anti-linear B type 6 and anti-B dissaccharide antibodies were present in every preparation of antibodies tested (Table 1). Based on the ELISA assay, these anti-linear B type 2, anti-linear B type 6 and anti-B dissaccharide antibodies appear to be the most significant group of anti-pig carbohydrate antibodies.

Antibodies capable of binding to A-related structures were expected since numerous papers have been published on many A or A-like glycolipids and glycoproteins isolated and/or characterized from swine tissue. A and O phenotypes have been reported in pigs (Holgersson et al. 1990[12]) and significant levels of anti-A are found in serum and plasma of humans with O or B phenotypes. Some of the O.D. readings for antibodies capable of binding to synthetic A structures were lower than expected. For example, for human O plasma anti-pig kidney (sample 8A° in Table 1), the pig had an A-phenotype based on agglutination of pig erythrocytes with human anti-A blood typing reagent, but the O.D. readings were less than 0.2 for A trisaccharide, A type 4, A type 5 and A type 6. The O.D. readings for human O plasma anti-pig kidney (sample 7B° in Table 1), however, were relatively high against A trisaccharide, A type 4, A type 5, and A type 6 (O.D.>1.0).

In most of the human anti-pig heart preparations some of the highest readings were against N-acetyl-β-D-glucosaminide (βGlcNAc), βGlcNAc(1-4)βGlcNAc, α-L-Rhamnose (α-L-Rha) and α-L-Rha(1-3)βGlcNAc(1-2)α-L-Rha (Table 1). There may be certain populations of anti-carbohydrate xenoantibodies that are more important for some organs.

Some of the monosaccharide and oligosaccharide structures that bound significant levels of human antibodies eluted from pig heart, pig kidney and/or pig red cell stroma (optical density at 405 nm≧0.5 after 1 hour) from one or more preparation are listed in Table 1.

There were variations in the carbohydrate structures which appeared to have fairly high antibody binding (O.D. at 405 nm≧0.5) from preparation to preparation. The type of human plasma, the individual plasma, the individual animal and/or the organ from which the antibodies were eluted all appeared to create variation.

The findings set forth in this application will apply to other organs and cells that have not been investigated. One specific embodiment contemplated by this invention is its use in conjunction with pancreatic islet cell xenotransplantation.

EXAMPLE 2

Measuring Human Hemolytic Antibodies to Porcine, Bovine and Sheep Erythrocyte Antigens Heat-Inactivation of serum and plasma for Examples 2, 3 and 4

Heat inactivated human serum or human plasma was used unless otherwise noted. It was heated in a water bath at 56° C. for 30 minutes to inactivate the complement (heat-inactivated).

Preparation of Serum for Example 2

Portions (1.2 ml) of human Type O serum were then transferred into test tubes containing 0.4 g±0.01 g of Chromosorb P (Manville Corp., Denver, Colo.), synthetic carbohydrate structures bound to Chromosorb P (hereinafter called SYNSORB, trademark of Chembiomed Ltd.), or mixtures of carbohydrate structures bound to Chromosorb P (mixtures of SYNSORB); and 0.3 ml PBS. Example 6, infra, describes the technique for coupling the carbohydrates to Chromasorb P as applied to compound 2 of FIG. 1A. The samples were mixed and incubated at 4° C. for 16 hours. These preparations were centrifuged at 1000 rpm and the supernatants collected.

Preparation of erythrocytes

Pig, bovine and sheep erythrocytes were washed 3 times with excess PBS (using a 1 minute centrifugation at 1000×g after each wash), then washed 3 times with 1% BSA in PBS. The final cell pellet was diluted to 1% (v/v) in 1% BSA in PBS.

Hemolytic assay

A hemolytic assay was then performed based on an assay described by Rapp and Borsos (1966)[21]. The adsorbed and unadsorbed serum samples were diluted 1/4 in 1% BSA in PBS, then 50 µl was added to the appropriate wells (FIG. 2 results); or adsorbed and unadsorbed human serum samples were undiluted or diluted 1/2 or 1/4 with 1% BSA in PBS, then 100 µl added to the appropriate wells (FIG. 3 results). A 1% suspension of porcine erythrocytes (FIG. 2) or a 2% suspension of porcine, sheep or bovine erythrocytes (FIG. 3) was added to the appropriate wells of a V shaped 96 well microtitration plate(s). Several control wells were also prepared containing 50 µl of erythrocyte suspension and 50 µl or 100 µl of 1% BSA in PBS. After a 1 hour incubation at 22° C. the plate(s) were centrifuged for 5 minutes at 1100 rpm in a Beckman TJ-6 Centrifuge (Beckman Instruments, Inc., Palo Alto, Calif., U.S.A.). A complement preparation was prepared using 1 ml of lyophilized LOWTOX-M rabbit complement (Cedarlane Laboratories Ltd., Hornby, Ontario, Canada) reconstituted with 1 ml of cold, purified water, then diluted 1/15 with gelatin veronal buffer (Sigma Chemical Co.). The supernatants were removed, then 200 µl of diluted complement, gelatin veronal buffer, or water was added to the wells. The samples were mixed using a clean pipette tip for each well, then incubated for 1 hour at 37° C. The plate(s) was centrifuged at 2000 rpm for 3 minutes, then 150 µl of supernatant/well was transferred into a flat-bottomed plate and the optical density at 405 nm (O.D.) was read using a Microplate Autoreader (Model EL 309, BIO-TEK Instruments, Winooski, Vt., U.S.A.).

The percentage (%) hemolysis was calculated based on: 0% hemolysis=the average O.D. from wells to which erythrocytes, 1% BSA in PBS and complement were added (no serum); and 100% lysis=the average O.D. from wells to which erythrocytes, unadsorbed serum or serum absorbed with Chromosorb P and complement were added.

Figure 2:
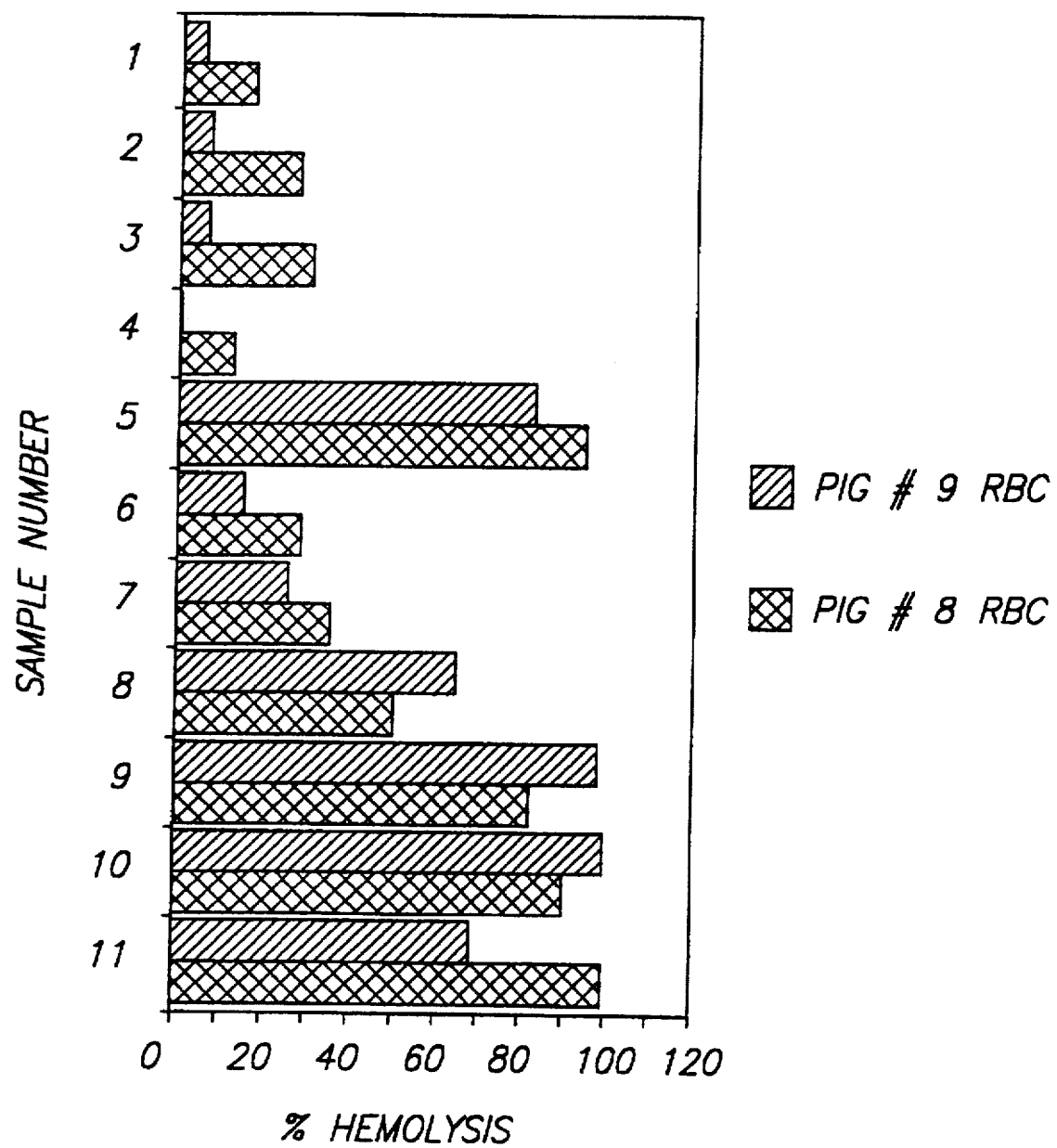
FIG. 2 illustrates that antibody-mediated lysis of pig erythrocytes is reduced by preadsorption of human plasma on a variety of matrix-bound carbohydrates and mixtures of matrix-bound carbohydrate structures.
Figure 3:
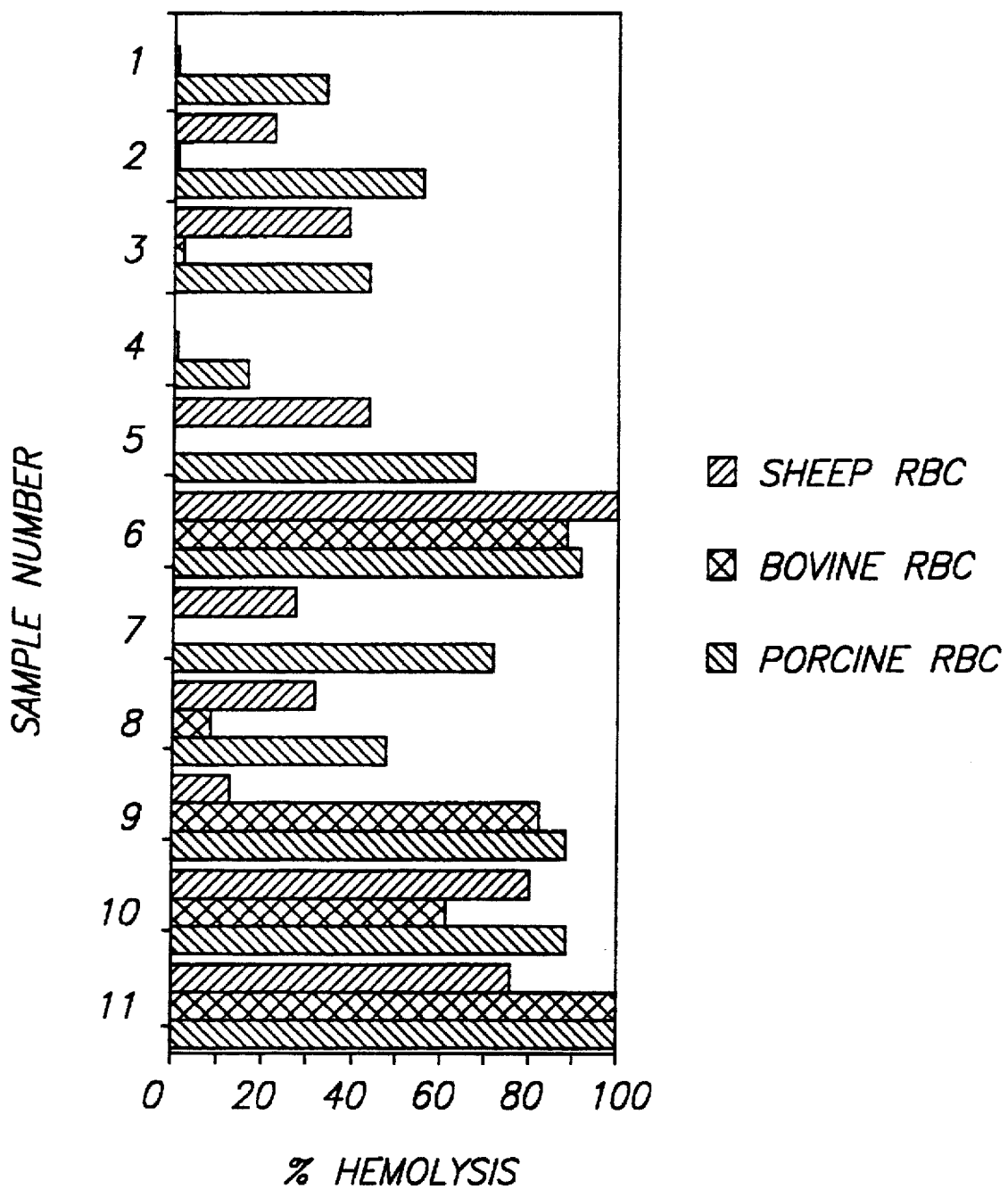
FIG. 3 illustrates that antibody-mediated lysis of sheep, pig and bovine erythrocytes is reduced by pre-adsorption of human plasma with matrix-bound carbohydrate and mixtures of matrix-bound carbohydrate structures.

Adsorption of human serum with particular carbohydrate structures bound to matrix and combinations of matrix-bound carbohydrates reduced the hemolysis of porcine, sheep and bovine erythrocytes (FIGS. 2 and 3).

The samples in FIG. 2 were adsorbed with the following SYNSORB-bound carbohydrates: a combination of linear B type 6, A trisaccharide, B trisaccharide and βGlcNAc (1); a combination of linear B type 6 and βGlcNAc (2); a combination of linear B type 6 and B trisaccharide (3); a combination of linear B type 6 and A trisaccharide (4); βGlcNAc (5); linear B type 2 linear B type 6 (7); B trisaccharide (8); A trisaccharide (9); LacNAc (10); and Chromosorb P alone (11). Structures are shown in FIG. 1A to 1H.

The samples in FIG. 3 were adsorbed with the following SYNSORB-bound carbohydrates: a combination of linear B type 6, A trisaccharide, B trisaccharide and βGlcNAc (1); a combination of linear B type 6 and B trisaccharide (2); a combination of linear B type 6 and βGlcNAc (3); a combination of linear B type 6 and A trisaccharide (4); linear B type 2 (5); βGlcNAc (6); linear B type 6 (7); B trisaccharide (8); A trisaccharide (9); LacNAc (10); and Chromosorb P alone (11).

As shown in FIG. 3, the combination of A trisaccharide-SYNSORB and linear B type 6-SYNSORB were more effective at reducing hemolytic activity to porcine and sheep erythrocytes than either linear B type 6-SYNSORB or A trisaccharide separately. Not all sera have anti-A activity and there is some diversity in the specificity and concentration of antibodies from individuals with various blood types and between individuals with the same blood type. Therefore it may be necessary to employ a combination of monosaccharides and/or oligosaccharides to reduce the majority of cytolytic antibodies. This would be the best combination of carbohydrate structures from person to person, from species to species, and from organ to organ.

EXAMPLE 3

Removal of Human Cytotoxic Antibodies to Pig Antigens with Matrix-Bound Carbohydrates In this experiment, pig erythrocytes, lymphocytes and an adherent pig kidney cell line (LLC-PK$_1$ from American Type Culture Collection, Rockville, Md., U.S.A.: Cat.#CRL 1392-CL101) were used as target cells. The erythrocytes and lymphocytes were separated from whole heparinized pig blood with Ficoll-Paque (Pharmacia LKB Biotechnology Inc., Piscataway, N.J., U.S.A.: Cat.#17-0840-02). The pig kidney cell line was cultured in Medium 199 (Gibco BRL Canada, Burlington, Ontario, Canada) with 10% FBS (Hybri-Max from Sigma Chemical Co.: Cat.#CPSR-3). Each of these target cells was labelled with chromium-51 (Amersham, Oakville, Ontario, Canada: Cat.#CJS.11) by incubation at 37° C. for 1 hour ($10^6$ cells with 100 µl (100 µCi) of chromium). Cells were washed once in medium, incubated for 1 hour at 37° C., and then washed twice to remove non-incorporated chromium.

Undiluted heat-inactivated plasma (100 µl) was incubated with 100 µl of chromium-labelled target cells ($2 \times 10^4$ cells) in 96 well V bottom microtiter plates (Dynatech Lab., Chantilly, Va., U.S.A.: Cat.#1-220-25X) at 37° C. for 1 hour with shaking (20 rpm). A 1/15 dilution of rabbit complement (LOWTOX-M from Cedarlane Laboratories Ltd., Hornby, Ontario, Canada: Cat.#(L3051) was added to each well. The plate was again incubated for 1 hour at 37° C. with shaking. Plates were then spun at 1000 rpm and supernatants were counted for chromium content in the Beckman gamma 4000 counter (Beckman Instruments, Inc., Fullerton, Calif., U.S.A.). Spontaneous and total release controls were also run. Spontaneous counts were always less than 5% of the total counts, and typical total counts of cells ranged from 10,000 to 20,000 cpm.

Figure 4A:
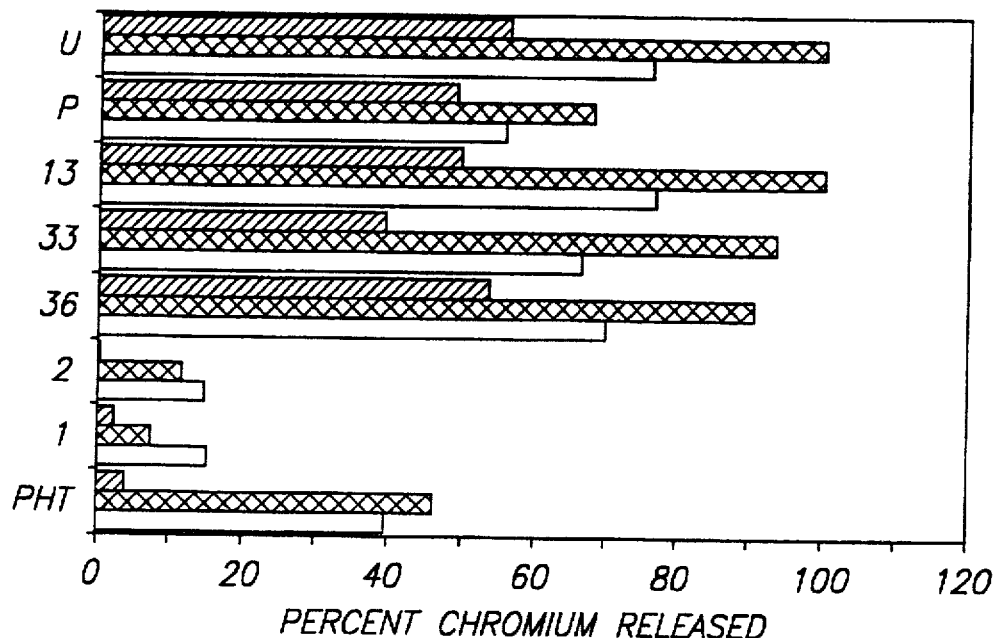
FIGS. 4A and 4B illustrate a reduction in lysis of a variety of pig cell types when human plasma {O plasma (A) and AB plasma (B)} were pre-adsorbed with matrix-bound αGal(1-3)βGal(1-4)βGlcNAc-R (linear B type 2) or αGal(1-3)βGal(1-4)βGlc-R (linear B type 6).
Figure 4B:
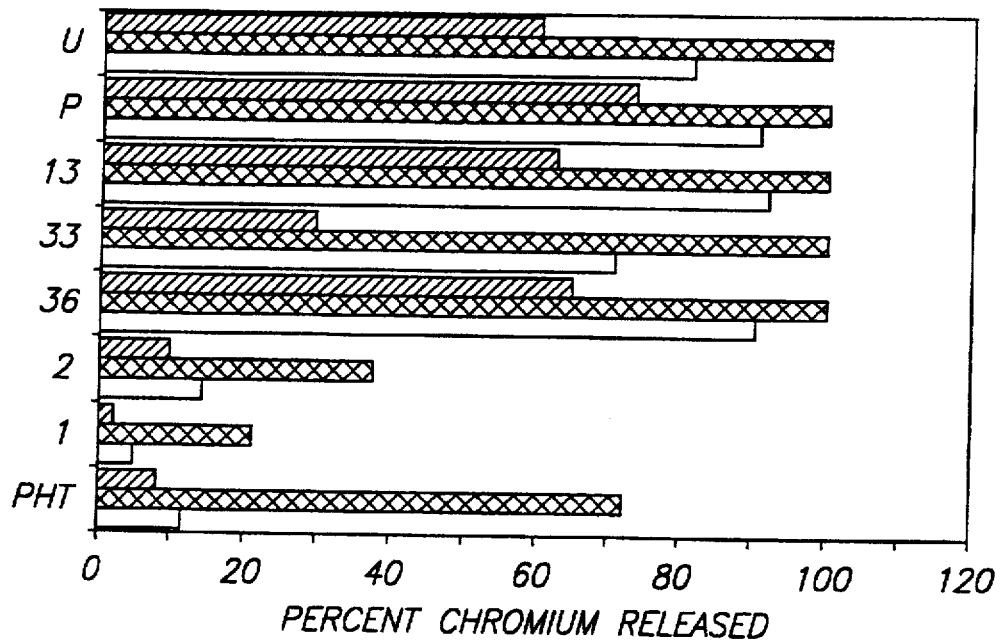
Figure 5:
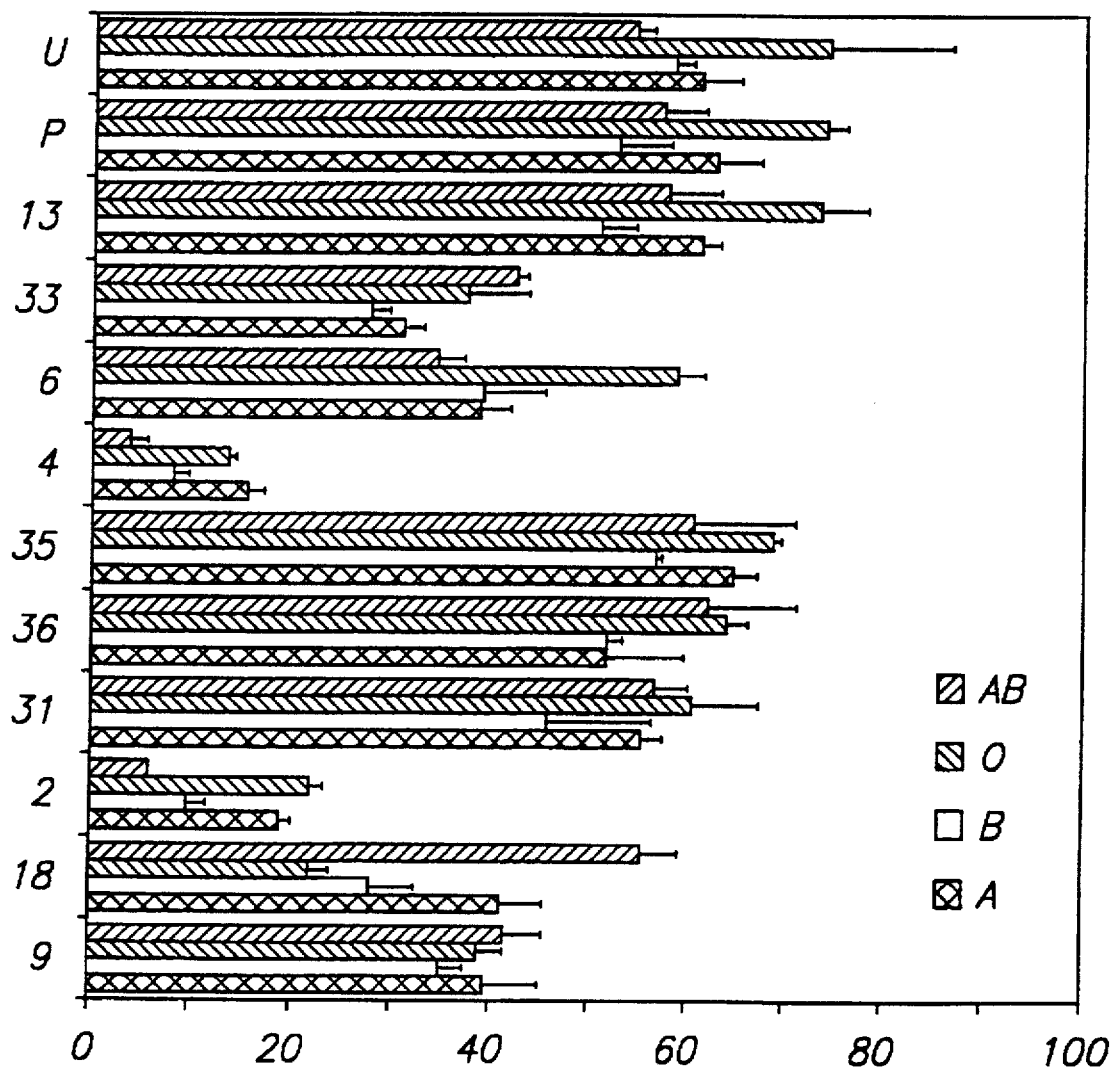
FIG. 5 illustrates a reduction in lysis to a pig kidney cell line (LLC-PK$_1$) when human plasma (O, A, B and AB) were preadsorbed with some matrix-bound carbohydrate antigens (formulas 2, 4, 6, 9, 13, 18, 31, 33, 35, and 36 of FIGS. 1A, 1B, 1C, 1D, 1G and 1H).

As seen from the results shown in FIGS. 4A and 4B, unadsorbed human O and AB plasma contained antibodies capable of lysing chromium-labelled pig lymphocytes, erythrocytes, and the pig kidney cell line. Perfusion of these plasma samples through the heart reduced cytotoxic activity (FIGS. 4A and 4B) presumably due to the binding of cytotoxic antibodies to the pig tissues. In a transplant situation, the binding of these antibodies could potentially cause hyperacute rejection.

To investigate the ability of the carbohydrates (A trisaccharide, B trisaccharide, LacNAc (βGal(1-4)βGlcNAc-R), linear B type 2 and linear B type 6), coupled onto SYNSORB, to remove human anti-pig cytotoxic antibodies, 1 ml of plasma was adsorbed overnight at 4° C. with 0.2 g of the different SYNSORB. The adsorbed plasma was then tested in the chromium release assay. The A trisaccharide-SYNSORB, B trisaccharide-SYNSORB, LacNAc-SYNSORB and Chromosorb P had little effect in these examples (FIGS. 4A and 4B). Linear B type 2-SYNSORB and linear B type 6-SYNSORB significantly reduced the cytolytic activity. These results clearly demonstrate that linear B type 2 or linear B type 6 bound to SYNSORB is effective in binding human anti-pig cytotoxic antibodies.

The following experiments were conducted using the experimental procedures described above, except that the plasma used were not heat inactivated. Rabbit complement was added to each well, as described previously.

Human plasma (A, B, O and AB) samples were adsorbed with matrix-bound carbohydrates (SYNSORBS) to remove human anti-pig cytotoxic antibodies. (Refer to FIGS. 1A to 1H for structures of the carbohydrate compounds used.) The adsorbed plasma were tested in the chromium release assay. These results, shown in FIG. 5, clearly demonstrate that the B disaccharide (formula 4 from FIG. 1A) and Linear B type 6 (formula 2 from FIG. 1A) SYNSORBS significantly reduce the cytotoxic activity in all human blood groups.

Figure 6:
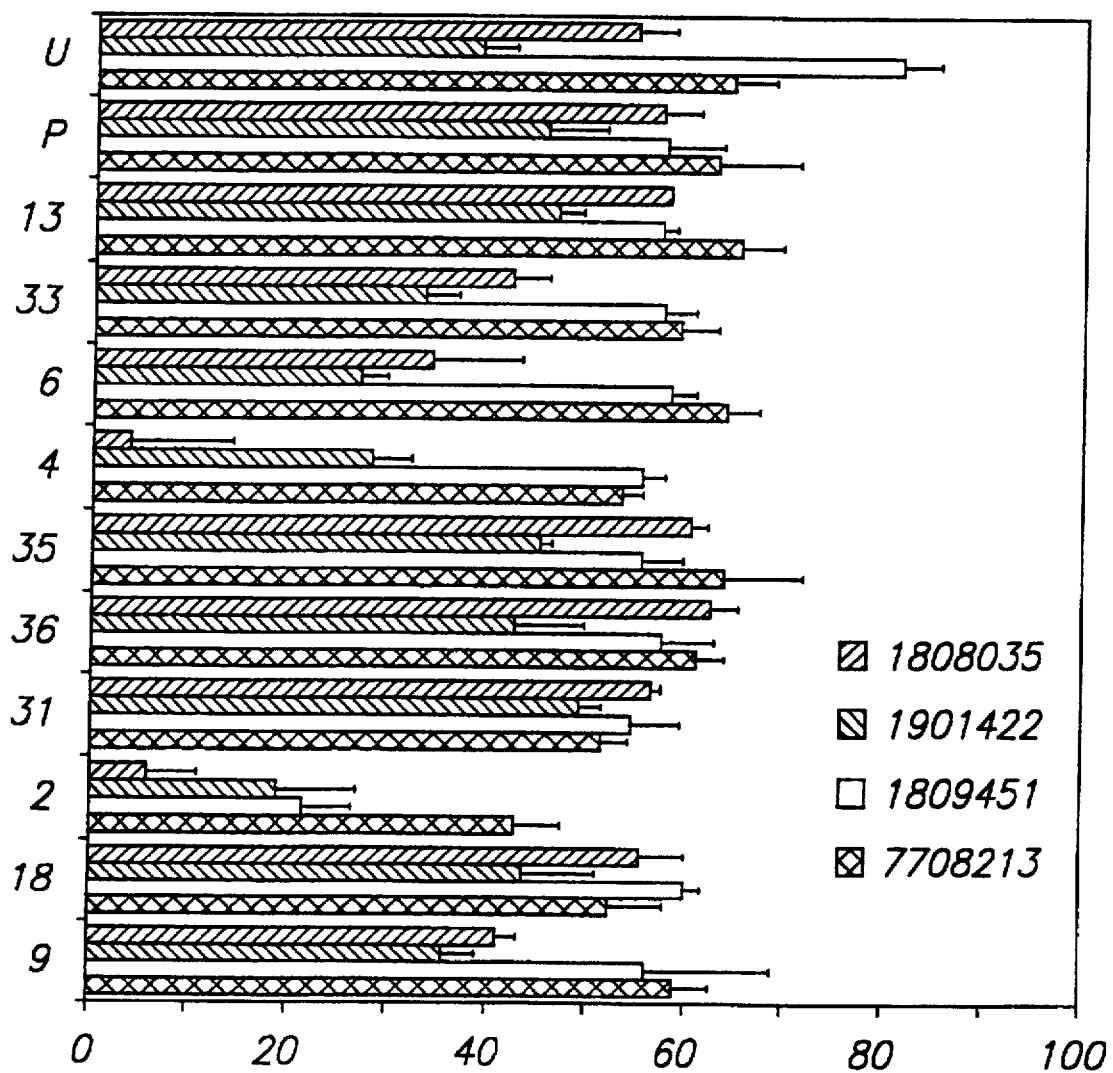
FIG. 6 illustrates a reduction in lysis to a pig kidney cell line (LLC-PK$_1$) when different human AB plasma were preadsorbed with some matrix-bound carbohydrate antigens.

Four different AB human plasma types were adsorbed with matrix-bound carbohydrates (SYNSORBS) to remove human anti-pig cytotoxic antibodies. (Refer to FIG. 1A to 1H for structures of the carbohydrate compounds used.) The adsorbed plasma were tested in the chromium release assay. Results are shown in FIG. 6. The B disaccharide and Linear B type 6 SYNSORBS significantly reduced the cytotoxic activity in one particular AB plasma (1808035). In another plasma sample (1901422), these SYNSORBS showed only marginal reduction of cytotoxic activity. In sample 1809451, the linear B type 6 SYNSORB reduced cytotoxic activity, but the B disaccharide SYNSORB did not. In sample 7708213, neither the B disaccharide SYNSORB nor the linear B type 6 SYNSORB significantly decreased cytotoxic activity. This example demonstrates heterogeneity in the population, since the cytotoxic antibodies found in some plasma apparently require adsorption by the αGal(1-3)βGal (1-4)βGlc structure while the Linear B backbone of the B disaccharide (αGal(1-3)βGal) is sufficient for adsorption of the cytotoxic antibodies in other plasma.

Figure 7:
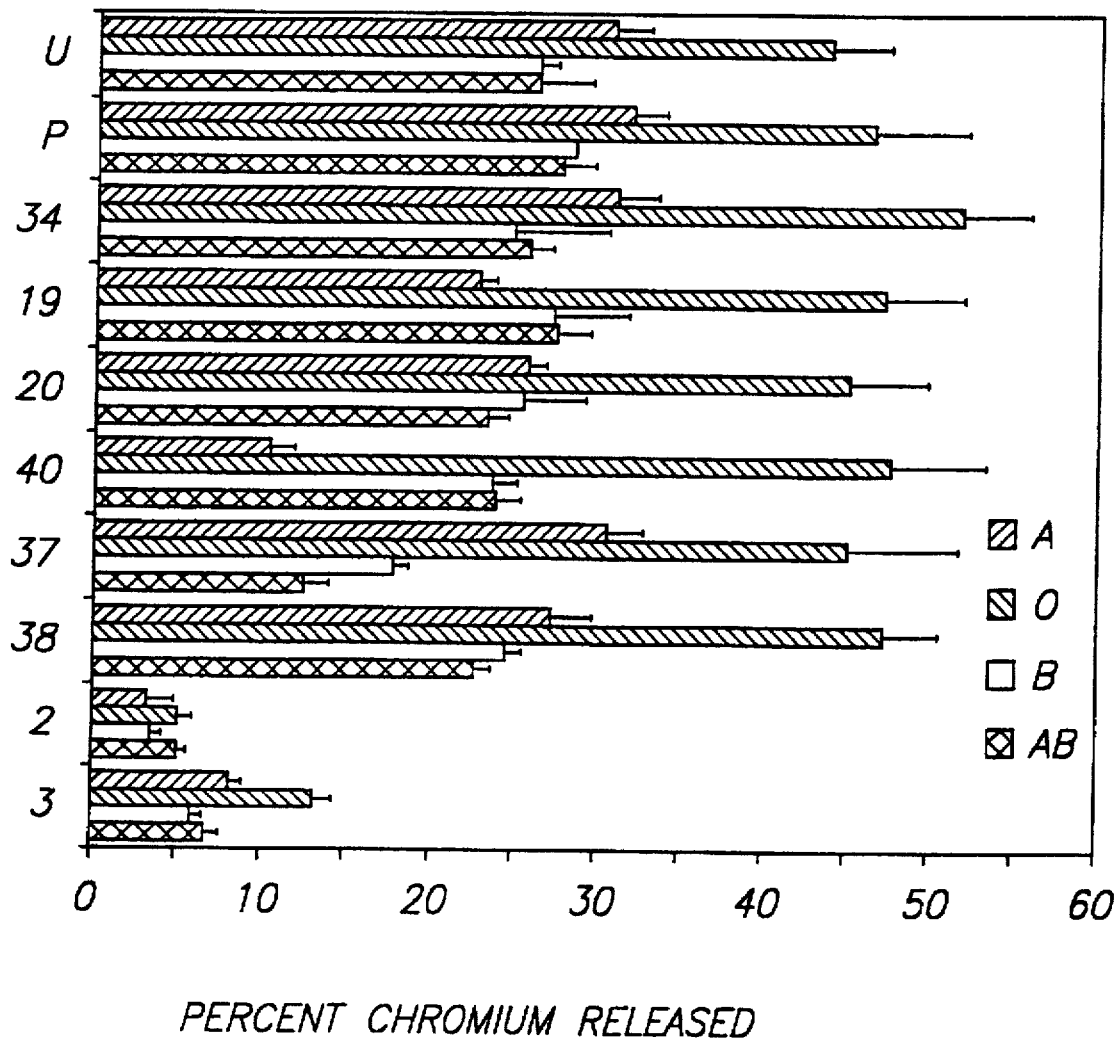
FIG. 7 illustrates a reduction in lysis to a pig kidney cell line (LLC-PK$_1$) when human plasma (O, A, B and AB) were preadsorbed with some matrix-bound carbohydrate antigens (formulas 2, 3, 19, 20, 34, 37, 38 and 40 of FIGS. 1A, 1E, 1G, and 1H).

Human plasma (A, B, O, and AB) samples were adsorbed with matrix-bound carbohydrates (SYNSORBS) to remove human anti-pig cytotoxic antibodies. (Refer to FIGS. 1A to 1H for structures of the carbohydrate compounds used.) The adsorbed plasma were tested in the chromium release assay. The results are shown in FIG. 7. Linear B type 6 and Linear B type 1 (formula 3 from FIG. 1A) SYNSORBS significantly reduced the cytotoxic activity in human plasma samples. P-K trisaccharide (formula 37 from FIG. 1H) SYNSORB marginally reduced cytotoxic activity in the Type AB and B human plasma tested. P-1 trisaccharide (formula 40 from FIG. 1H) SYNSORB marginally reduced cytotoxic activity in this Type A human plasma. P-K and P-1 trisaccharide SYNSORBS did not show reduction of cytotoxic activity in this Type O human plasma. These results show that the Linear B structure is specific for cytotoxic antibodies, but other carbohydrates may remove or block other antibody specificities.

EXAMPLE 4

Figure 8A:
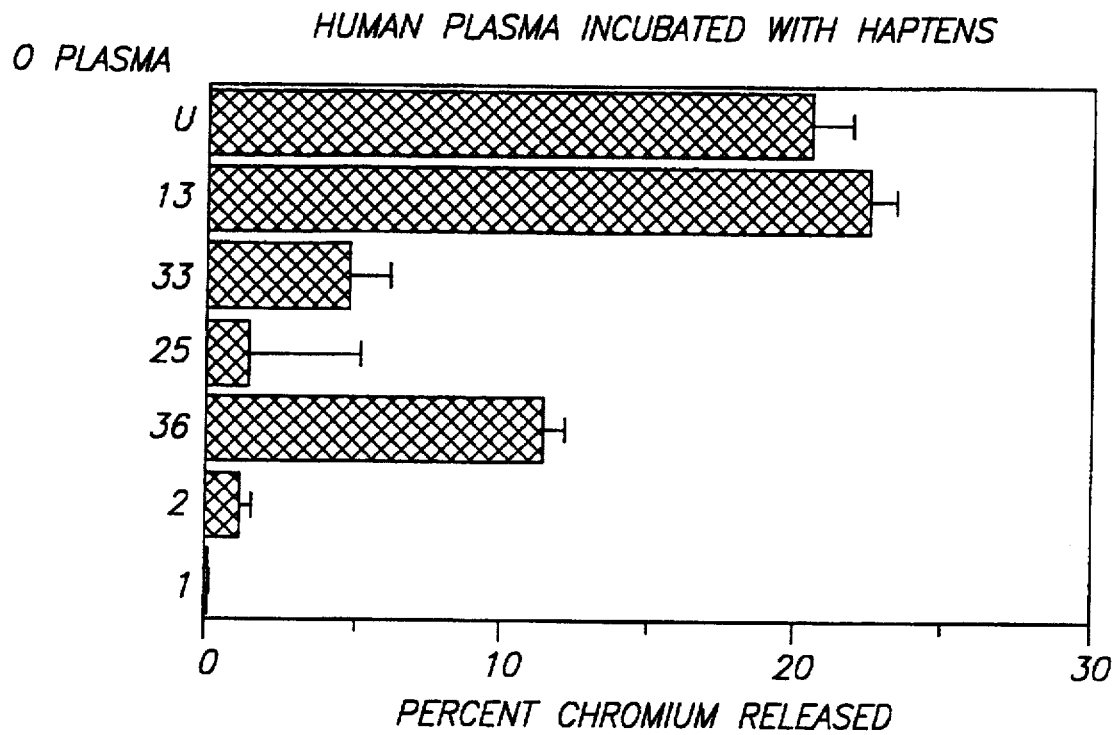
FIGS. 8A and 8B illustrate a reduction in lysis to a pig kidney cell line (LLC-PK$_1$) when human plasma {O plasma (A) and A plasma (B)} were incubated with some soluble carbohydrate antigens.
Figure 8B:
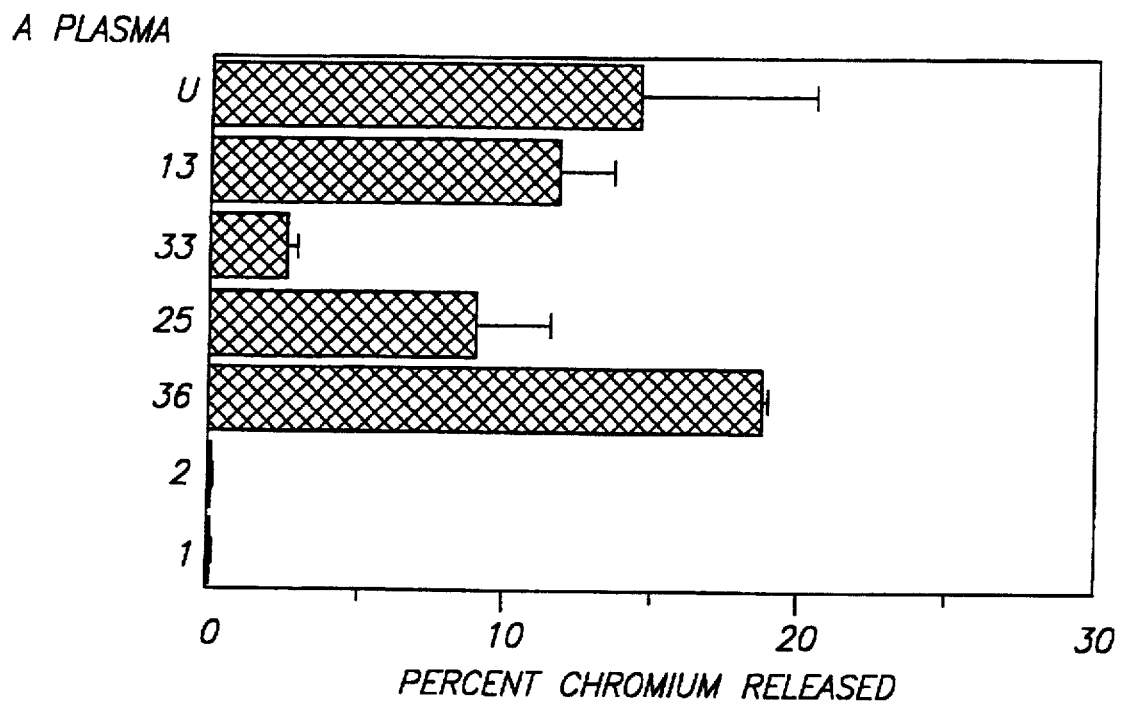

Removal of Human Cytotoxic Antibodies to Pig Antigens with Carbohydrate Haptens This procedure was done to investigate the potential for inhibiting human preformed cytotoxic antibodies with carbohydrate(s) haptens. Human heat inactivated plasma (1 ml) was incubated overnight at 4° C. with 0.215 g of A-trisaccharide-X-Y, B-trisaccharide-X-Y, βGlcNAc-X-Y, LacNAc-X-Y, linear B type 2-X-Y, or linear B type 6-X-Y (X-Y=—O—$(CH_2)_8$—$COOCH_3$ or —O—$(CH_2)_8$—$COOCH_2CH_3$, as in FIGS. 1A to 1H, referred to as SYNJECT, trademark of Chembiomed, Ltd.). The chromium release assay was then performed with treated and untreated plasma; the pig kidney cell line ($LLC-PK_1$) was used as the target cell. As depicted in FIGS. 8A and 8B, linear B type 2-X-Y and linear B type 6-X-Y completely inhibited the cytotoxic effect of antibodies to the pig cell line. Other haptens partially inhibited these cytotoxic antibodies (i.e., B trisaccharide). These results indicate that a soluble carbohydrate(s) hapten (SYNJECT form) may be effective for in situ inhibition of pre-formed human anti-carbohydrate antibodies.

The following experiments were conducted using the experimental procedures described above, except that the plasma used were not heat inactivated. Rabbit complement was added to each well, as described above in Example 3.

Figure 9:
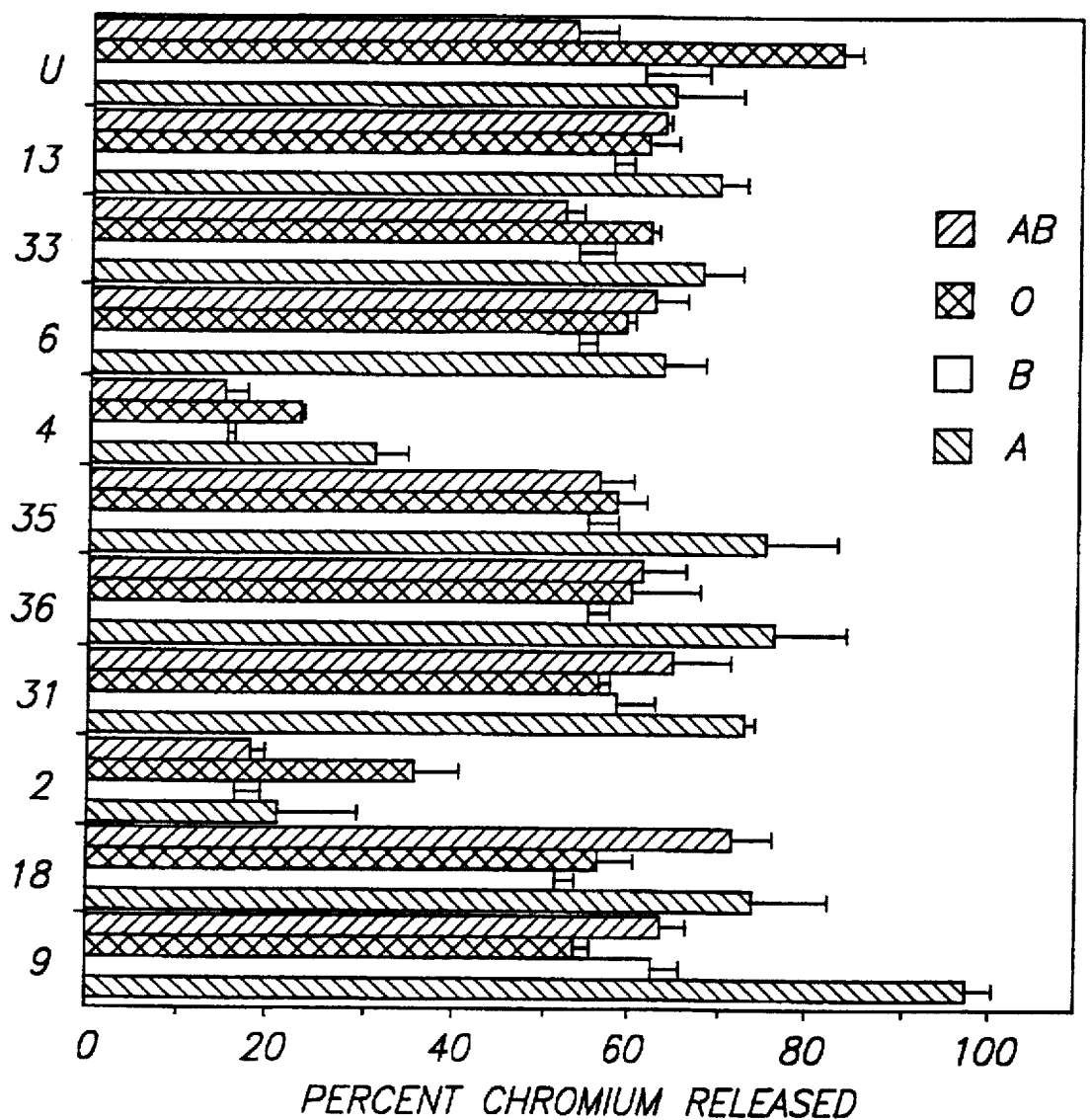
FIG. 9 illustrates a reduction in lysis to a pig kidney cell line (LLC-PK$_1$) when human plasma (O, A, B and AB) were incubated with some soluble carbohydrate antigens.

Human plasma (A, B, O, and AB) samples were incubated with carbohydrate haptens to inactivate human anti-pig cytotoxic antibodies. (Refer to FIGS. 1A to 1H for structures of the carbohydrate compounds used.) The incubated plasma were tested in the chromium release assay. Results are shown in FIG. 9. B disaccharide and Linear B type 6 haptens significantly reduced the cytotoxic activity in all blood groups.

Figure 10:
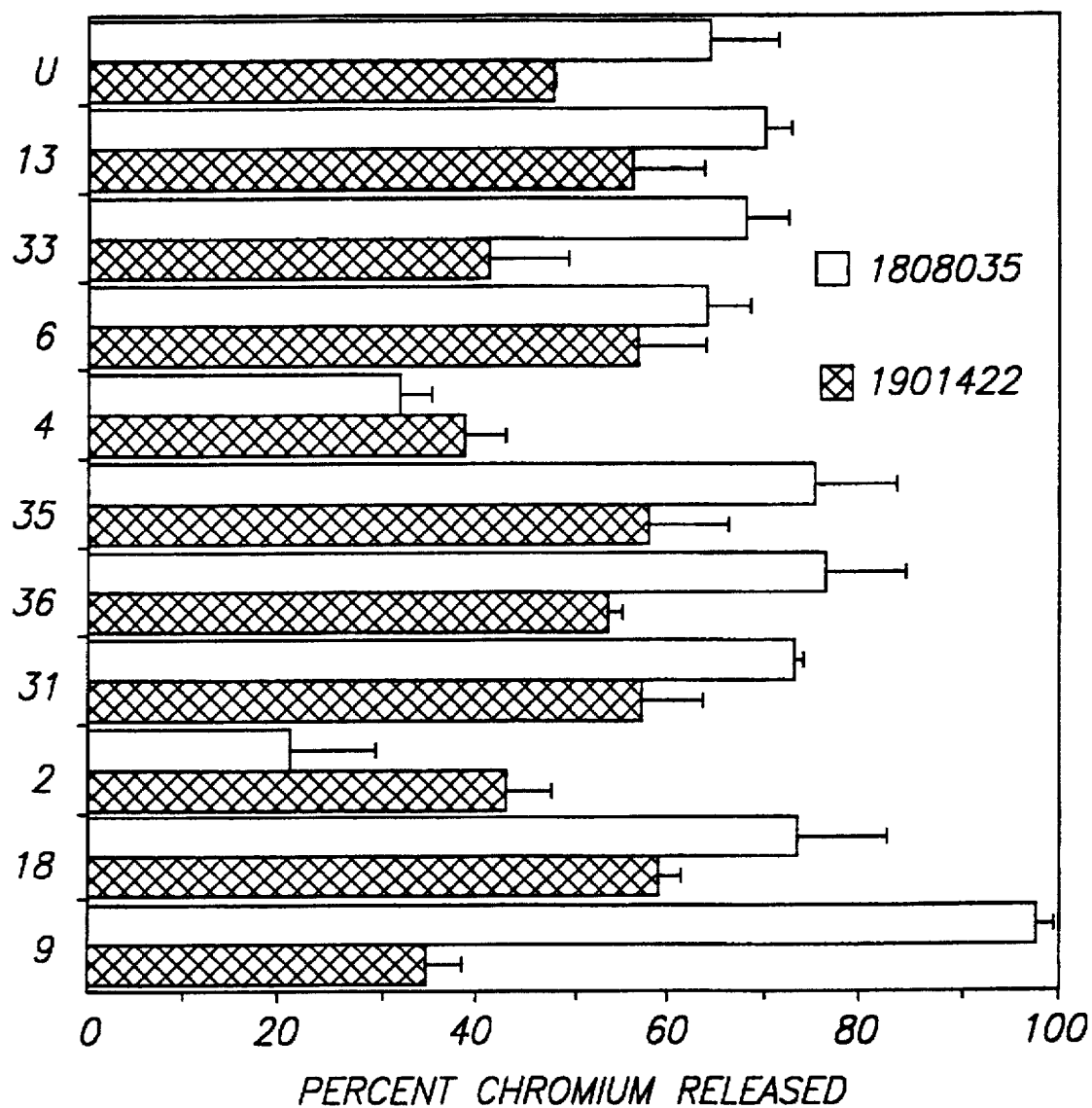
FIG. 10 illustrates a reduction in lysis to a pig kidney cell line (LLC-PK$_1$) when different human AB plasma were incubated with some soluble carbohydrate antigens.
Figure 12B:
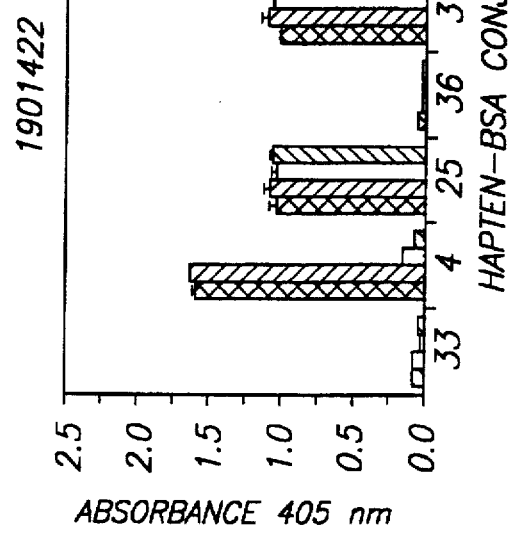
FIGS. 12A–12D illustrate removal of antibodies when different human AB plasma were preadsorbed with some matrix-bound carbohydrate antigens as detected by ELISA.
Figure 12D:
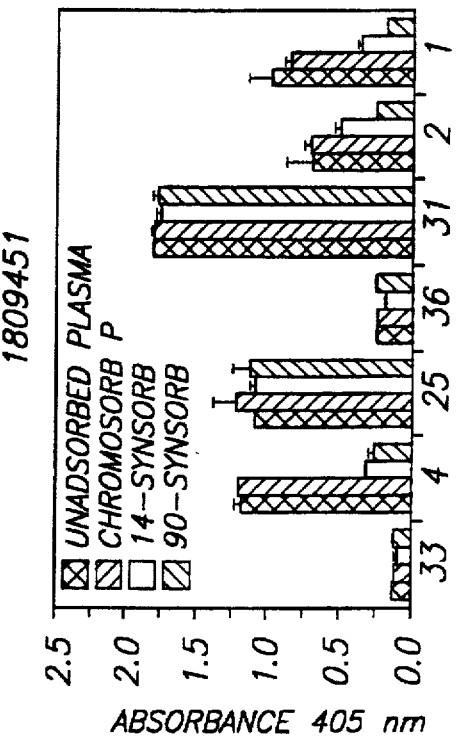
Figure 12A:
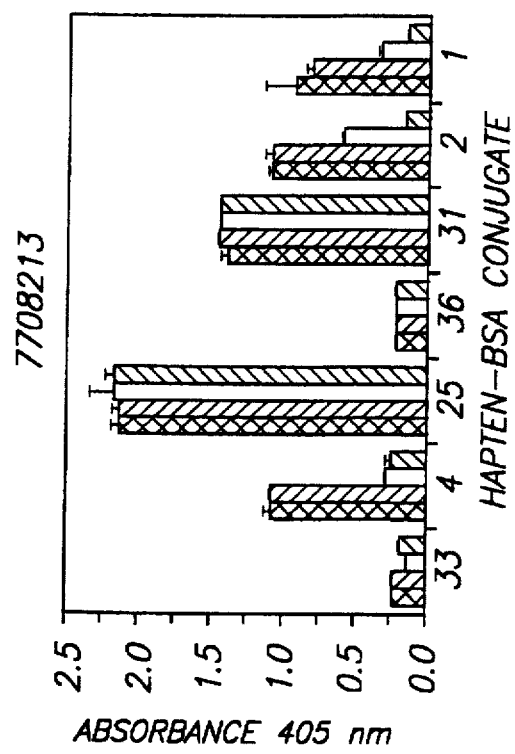
Figure 12C:
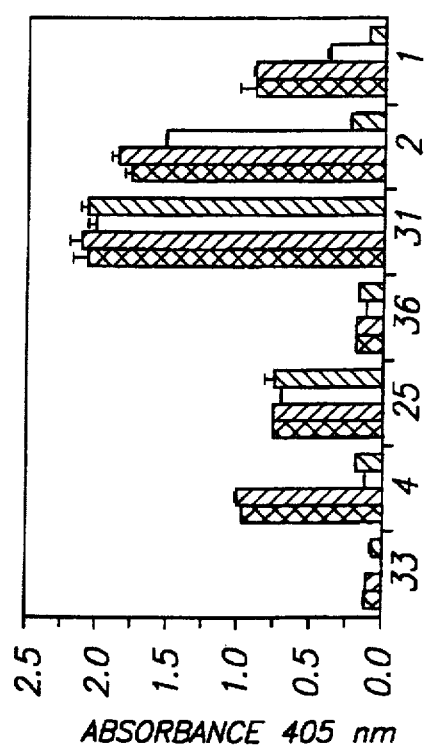

Two different AB human plasma types were incubated with carbohydrate haptens to remove human anti-pig cytotoxic antibodies. (Refer to FIGS. 1A to 1H for structures of the carbohydrate compounds used.) The incubated plasma were tested in the chromium release assay. The results are shown in FIG. 10. B disaccharide hapten only marginally reduced the cytotoxic activity in both plasma types. Linear B type 6 and B type 6 haptens each reduced the cytotoxic activity in one plasma type, but not the other. This example further demonstrates heterogeneity in the population.

EXAMPLE 5

Preparing (αGal(1-3)βGal(1-4)βGlc-O-$(CH_2)_8$CONH)$_{17}$-BSA

Sixty milligrams of the methyl ester form of compound 2 in FIG. 1 (αGal(1-3)βGal(1-4)βGlc-O-$(CH_2)_8COOCH_3$) was dissolved in 1.5 ml of hydrazine hydrate. After 2 hours, the hydrazine hydrate was removed in high vacuum and the residue was co-evaporated with water, then the hydride was purified on a C18 reverse phase column (Waters Chromatography Division, Millipore Corp., Milford Mass., U.S.A.) then freeze-dried. Nineteen mg of the synthetic hapten hydride was dissolved in 0.2 ml dry amine-free DMF and cooled to −20° C. under an inert atmosphere. A 3.6M solution (31 µl) of HCl in dioxane and 5.3 µl (45 µmoles) of tertiary butyl nitrite were added and the solution stirred for 30 minutes at 20° C. Sulfamic acid (1.4 mg) in DMF was added and stirred for an additional 15 minutes. This acyl azide solution was added directly to a solution of (30 mg BSA in 3 ml 0.2M N-thioldiethanolamine in water, pH 8.98, 0° to 4° C.). After 16 hours at 4° C., the solution was dialyzed against water, then freeze dried. Thirty-six mg of a white powder was recovered. The incorporation of hapten was determined by the phenol-sulfuric acid method (Dubois et al. 1956[5]) and was calculated to be 17 moles of hapten per mole of BSA.

This preparation was used in Example 1 to detect anti-linear B type 6 antibodies.

EXAMPLE 6

Preparation of an Effective Immunoadsorbent (αGal (1-3)βGal(1-4)βGlc—O—$(CH_2)_8$CONH)- SYNSORB Forty mg of the hydride form of compound 2, in FIG. 1A was prepared as described in Example 5 and dissolved in 0.3 ml DMF. This solution was cooled to −20° C. under an inert atmosphere. A 3.6M solution (62 µl) of HCl in dioxane and 11 µl (90 µmoles) of tertiary butyl nitrite were added and the solution stirred for 30 minutes. Hunigs base (N,N-Diisopropylethylamine from Aldrich Chemical Co., Inc., Milwaukee, Wis. U.S.A.: Cat.#D12.580.6) (45 µl or 258 µmoles) was added and stirred for an additional 2 minutes. This acyl azide solution was added directly to a slurry of silylaminated calcined diatomaceous earth (56 g of Chromosorb P from Manville Corp., Denver, Colo.) in acetonitrile (150 ml) at 4° C. (The silylamination was performed using a protocol described by Weetall (1976)[24].) After stirring for 2 hours at 4° C. and 2 hours at room temperature, the solid was collected by filtration and the unreacted amines were N-acetylated using 5% acetic anhydride in methanol, gently stirred for one hour, then incubated overnight at room temperature. The solid portion was then washed using methanol and ethyl ether, then air dried. The incorporation of hapten was determined by the phenol-sulfuric acid method and determined to be 0.87 µmole of hapten/g of matrix.

This preparation was used in Examples 2 and 3 to remove anti-linear B type 6 antibodies.

EXAMPLE 7

Detection of a Reduction of Human Antibody Titers to Carbohydrate Compounds by Plasma Adsorption with Matrix-Bound Carbohydrate(s) Using Enzyme-Linked Immunosorbent Assay (ELISA)

Flat-bottom 96 well immuno-plates (Gibco-BRL, Burlington, Ontario, Canada) were coated with 100 µl/well of 10 µg/ml BSA or carbohydrate-BSA conjugates diluted in 0.05M carbonate-bicarbonate coating buffer (Sigma Chemical Co.), pH 9.6. Plates were incubated at 4° C. for 18 hours, then emptied and blocked with 150 µl/well of 1% BSA (Sigma) in PBS for one hour at room temperature. The plates were then washed three times with PBS containing 0.05% polyoxyethylene-sorbitan monolaurate (tween 20; Sigma).

Human plasma from blood types A, B, AB, and O, either unadsorbed or adsorbed with Chromosorb P, B dissacharide SYNSORB, or Linear B type 6 SYNSORB were diluted 1:100 with PBS-tween 20 and aliquoted in triplicate to BSA control on carbohydrate-BSA coated wells. After an incubation period of two hours at room temperature and three subsequent washings with PBS-tween 20, all wells received 100 μl of goat anti-human polyvalent (α, γ, and μ chain specific)-alkaline phosphate conjugate (Sigma) diluted 1:350 in PBS-tween 20. Once again the plates were incubated at room temperature for two hours and then washed three times with PBS-tween 20. One hundred microliters of disodium p-nitrophenyl phosphate (Sigma) diluted to 1 mg/ml in 10% (v/v) diethanolamine buffer, pH 9.8 (Fisher Scientific), containing 0.01% (w/v) magnesium chloride (Fisher Scientific) was added to each well. The immunoplates were incubated in the dark at room temperature for 30 minutes. The absorbance at 405 nm was then read for each well using a Titertek Multiskan (Flow Laboratories, McLean, Va.). Measurements of non-specific binding of plasma to wells coated with BSA only, were subtracted from the results presented in FIGS. 11A–11D and 12A–12D.

Human A, B, O, and AB plasma adsorbed with SYN-SORBS were tested against a panel of Hapten-BSA conjugates. Refer to FIGS. 1A and 1H for structures of the carbohydrate compounds used. As shown in FIG. 11A–11D, plasma adsorbed with B dissacharide or Linear B type 6 SYNSORBS showed markedly decreased binding to the B dissacharide, Linear B type 6 and Linear B type 2 BSA conjugates when compared to unadsorbed plasma or plasma adsorbed with Chromosorb P. These SYNSORBS did not decrease binding to N-acetyl-β-D-Glucosaminide (formula 25 from FIG. 1F) and α-L-Rhamnose (formula 31 from FIG. 1H) BSA conjugates. These results demonstrate that B dissacharide and Linear B type 6 SYNSORBS were able to remove or reduce specific antibody from plasma.

Human AB plasma adsorbed with SYNSORBS were tested against a panel of Hapten-BSA conjugates. Refer to FIGS. 1A to 1H for structures of the carbohydrate compounds used. As shown in FIG. 12A–12D, plasma adsorbed with B dissacharide or Linear B type 6 SYNSORBS showed decreased binding to the B dissacharide, Linear B type 6 and Linear B type 2 BSA conjugates when compared to unadsorbed plasma or plasma adsorbed with Chromosorb P. These SYNSORBS did not decrease binding to other Hapten-BSA conjugates. These results demonstrate that B dissacharide and Linear B type 6 SYNSORBS were able to remove or reduce specific antibody from plasma.

Modifications of the above-described modes that are obvious to those of skill in the fields of transplantation immunology, carbohydrate chemistry, and related fields are intended to be within the scope of the following claims.

What is claimed is:

1. An immunoadsorbent composition useful for removing xenoantibodies from the blood of a human recipient of a xenograft to attenuate the rejection of the xenograft by the recipient comprising a biocompatible solid support having at least one identified carbohydrate xenoantigen comprising linear B type 6 to preformed antibodies attached thereto through a biocompatible linker arm.

2. The composition of claim 1 wherein the carbohydrate xenoantigen further comprises at least one of the glycosides having structures 3, 21, 23, 26, 27, 28, 29, 30, 31 and 32 of FIGS. 1A through 1H where X is selected from the group consisting of O, S, NH, and a bond and Y is an aglycon group.

3. The composition of claim 2 wherein Y represents the group consisting of —(A)—Z wherein A represents a bond, an alkylene group of from 2 to 10 carbons or —(CH$_2$—CR$_1$—G)$_n$—, wherein n is an integer equal to 1 to 5 inclusive; R$_1$ is selected from the group consisting of hydrogen, methyl and ethyl; and G is selected from the group consisting of hydrogen, oxygen, sulfur, nitrogen, phenyl, and phenyl substituted with 1 to 3 substituents selected from the group consisting of amine, hydroxyl, halo, and alkyl of from 1 to 4 carbon atoms, and Z is selected from the group consisting of hydrogen, methyl and when G is not oxygen, sulfur or nitrogen and A is not a bond, then Z is also selected from the group consisting of OH, SH, —NH$_2$, —NHR$_2$, —C(O)OR$_2$, —C(O)NH$_2$, —C(O)NH—NHR$_2$, —C(O)NHR$_2$ and —C(O)N(R$_2$)$_2$ wherein each R$_2$ is independently hydrogen or alkyl of from 1 to 4 carbon atoms.

4. The composition of claim 2 wherein X is —O— and Y is —A—Z where A is alkylene of 2 to 10 carbon atoms and Z is selected from the group consisting of —C(O)OR$_2$, —C(O)NH$_2$ and —C(O)NHR$_2$ where R$_2$ is hydrogen or alkyl of from 1 to 4 carbon atoms.

5. The composition of claim 1 wherein the carbohydrate xenoantigen further comprises the glycoside structure 1 of FIG. 1A and X is —O— and Y is —A—Z where A is alkylene of 2 to 10 carbon atoms and Z is selected from the group consisting of —C(O)OR$_2$, —C(O)NH$_2$ and —C(O)NHR$_2$ where R$_2$ is hydrogen or alkyl of from 1 to 4 carbon atoms.

6. The composition of claim 1 wherein the carbohydrate xenoantigen comprises the glycoside structure 2 of FIG. 1A and X is —O— and Y is —A—Z where A is alkylene of 2 to 10 carbon atoms and Z is selected from the group consisting of —C(O)OR$_2$, —C(O)NH$_2$ and —C(O)NHR$_2$ where R$_2$ is hydrogen or alkyl of from 1 to 4 carbon atoms.

7. The composition of claim 1 wherein the carbohydrate xenoantigen further comprises the glycoside structure 4 of FIG. 1A and X is —O— and Y is —A—Z where A is alkylene of 2 to 10 carbon atoms and Z is selected from the group consisting of —C(O)OR$_2$, —C(O)NH$_2$ and —C(O)NHR$_2$ where R$_2$ is hydrogen or alkyl of from 1 to 4 carbon atoms.

* * * * *